(12) United States Patent
Sampson et al.

(10) Patent No.: US 9,238,823 B2
(45) Date of Patent: Jan. 19, 2016

(54) PESTICIDAL GENES FROM BREVIBACILLUS AND METHODS FOR THEIR USE

(71) Applicant: Athenix Corporation, Morrisville, NC (US)

(72) Inventors: Kimberly S. Sampson, Durham, NC (US); Daniel J. Tomso, Bahama, NC (US); Rong Guo, Cary, NC (US)

(73) Assignee: Athenix Corp., Morrisville, NC (US)

( * ) Notice: Subject to any disclaimer, the term of this patent is extended or adjusted under 35 U.S.C. 154(b) by 222 days.

(21) Appl. No.: 13/779,524

(22) Filed: Feb. 27, 2013

(65) Prior Publication Data

US 2013/0167264 A1    Jun. 27, 2013

Related U.S. Application Data

(63) Continuation of application No. 12/644,632, filed on Dec. 22, 2009.

(60) Provisional application No. 61/139,947, filed on Dec. 22, 2008.

(51) Int. Cl.
| | | |
|---|---|---|
| *A01H 5/00* | (2006.01) | |
| *A01H 5/10* | (2006.01) | |
| *C12N 15/82* | (2006.01) | |
| *C07K 14/345* | (2006.01) | |
| *C12N 15/32* | (2006.01) | |
| *A01N 37/18* | (2006.01) | |
| *A01N 25/26* | (2006.01) | |
| *C07K 14/195* | (2006.01) | |
| *C07K 14/325* | (2006.01) | |

(52) U.S. Cl.
CPC .......... *C12N 15/8286* (2013.01); *C07K 14/195* (2013.01); *C07K 14/325* (2013.01); *C07K 14/345* (2013.01)

(58) Field of Classification Search
None
See application file for complete search history.

(56) References Cited

U.S. PATENT DOCUMENTS 7,091,399 B2 *   8/2006   Boets et al. ................... 800/279

FOREIGN PATENT DOCUMENTS

| EP | 1277763 | 1/2003 |
|---|---|---|
| WO | 0009697 | 2/2000 |
| WO | 01/87931 | 11/2001 |

OTHER PUBLICATIONS de Maagd, et al (Trends in Genetics, 2001, 17(4), pp. 193-199).
De Oliveira E.J., et al. Molecular characterization of Brevibacillus laterosporus and its potential use in biological control, Applied and Environmental Microbiology US, Nov. 2004, vol. 70, No. 11, pp. 6657-6664.
Favret, Montgomery E., et al., Insecticidal Activity of Bacillus laterosporus, Journal of Invertebrate Pathology, 1985, vol. 45, pp. 195-203.
Orlova Margarita V., et al., Insecticidal activity of Bacillus laterosporus, Applied and Environmental Microbiology, Jul. 1998, vol. 64, No. 7, pp. 2723-2725.
Prasanna, et al. (Appl. Microbiol Biotechnol, Apr. 29, 2012).
Ruiu Luca, et al., Lethal and Sublethal Effects of Brevibacillus Laterosporus on the Housefly (*Musca domestica*), Entomologia Experimentalis Et Applicata, Kluwer Academic Publishers, Dordrecht, NL, Feb. 2006, vol. 118, No. 2, pp. 137-144.
Ruiu, et al., Toxicity of a Brevibacillus Laterosporus Strain Lacking Parasporal Crystals Against *Musca domestica* and Aedes Aegypti, Biological Control, San Diego, CA, US, Sep. 2007, vol. 43, pp. 136-143.
Singer, Samuel, The Utility of Strains of Morphological Group II Bacillus, Advances in Applied Microbiology, vol. 42, pp. 219-261.
Tounsi, et al. (J. Appl Microbiol 95:23-28; 2003).
Zahner, Viviane, et al., Geontypic Diversity among Brevibacillus laterosporus Strains, Applied and Environmental Microbiology, Nov. 1999, vol. 65, No. 11, pp. 5182-5185.
Partial European Search Report for Application No. 13182993.9-1401 dated Jan. 17, 2014.
Partial International Search Report for PCT/US2009/069144, mailed Mar. 30, 2010 (3 pages).

\* cited by examiner

*Primary Examiner* — Lee A Visone

(57) ABSTRACT

Compositions and methods for conferring insecticidal activity to bacteria, plants, plant cells, tissues and seeds are provided. Compositions including a coding sequence for a *Brevibacillus*-derived delta-endotoxin polypeptide are provided. The coding sequences can be used in DNA constructs or expression cassettes for transformation and expression in plants and bacteria. Compositions also include transformed bacteria, plants, plant cells, tissues, and seeds. In particular, isolated delta-endotoxin nucleic acid molecules are provided. Additionally, amino acid sequences corresponding to the polynucleotides are encompassed, and antibodies specifically binding to those amino acid sequences. In particular, the present invention provides for isolated nucleic acid molecules having nucleotide sequences encoding the amino acid sequence shown in SEQ ID NO:2, 4, 7, or 10, or the nucleotide sequence set forth in SEQ ID NO:1, 3, 5, 6, 8, 9, 11, 12, 13, 14, or 15, as well as variants and fragments thereof.

21 Claims, No Drawings

PESTICIDAL GENES FROM BREVIBACILLUS AND METHODS FOR THEIR USE

CROSS REFERENCE TO RELATED APPLICATION

This application is a continuation of U.S. patent application Ser. No. 12/644,632, filed Dec. 22, 2009, which claims the benefit of U.S. Provisional Application Ser. No. 61/139,947, filed Dec. 22, 2008, the contents of which are herein incorporated by reference in their entirety.

REFERENCE TO SEQUENCE LISTING SUBMITTED AS A TEXT FILE VIA EFS-WEB

The official copy of the sequence listing is submitted concurrently with the specification as an ASCII formatted text file via EFS-Web, with a file name of "APA059SEQLIST.txt", a creation date of Feb. 27, 2013, and a size of 98 kilobytes. The sequence listing filed via EFS-Web is part of the specification and is hereby incorporated in its entirety by reference herein.

FIELD OF THE INVENTION

This invention relates to the field of molecular biology. Provided are novel genes that encode insecticidal proteins. These proteins and the nucleic acid sequences that encode them are useful in preparing insecticidal formulations and in the production of transgenic insect-resistant plants.

BACKGROUND OF THE INVENTION

*Brevibacillus* is a spore-forming bacterium that has been suggested for probiotic effects. For example, *Brevibacillus brevis* is now well established as a biocontrol agent in many areas, and has been shown to have efficacy against *Botrytis* and powdery mildew disease (Edwards and Seddon, Edwards and Seddon (1992) Recent Advances in *Botrytis* Research. The Netherlands: Pudoc Scientific Publications; *Bacillus brevis* as a Biocontrol Agent against *Botrytis cinerea* on Protected Chinese Cabbage; pp. 267-271) and *Fusarum* head blight (FHB) (Zhang et al. (2005) J Zhejiang Univ Sci B. 6(8):770-777). By comparing the activity of *B. brevis* Nagano against *Botrytis cinerea* with that of pure gramicidin S and the antibiotic-negative mutant *B. brevis* E-1, Edwards and Seddon ((2001) J Appl Microbiol. 91:652-659) showed that the mode of antagonism exhibited was antibiosis due to the presence of gramicidin S. There are some other antibiotics (for example tyrocidins and gramicidin D) reported to be produced by *B. brevis* (Saito et al., 1970, *Adv Enzymol.* 33:337-380).

*Brevibacillus laterosporus* comb. nov. (Shida (1996) Int. J. Syst. Bacteriol. 46:939-946), previously classified as *Bacillus laterosporus*, is an aerobic spore-forming bacterium that can also demonstrate pathogenicity to insects. In common with *B. sphaericus* and *B. thuringiensis, B. laterosporus* produces parasporal bodies, which in this species may be canoe-shaped and which serve to cradle the spore (Hanney (1957) J. Biophys. Biochem. Cytol. 3:1001-1010) or can even be present in different shapes (Smirnova et al. (1996) Res. Microbiol. 147:343-350). However, these parasporal bodies were not considered to have any entomocidal activity (Favret and Yousten (1985) J. Invertebr. Pathol. 45:195-203) until Orlova et al. ((1998) Appl. Environ. Microbiol. 64:2723-2725) demonstrated that some crystals produced during sporulation are highly toxic to *Aedes aegypti* and *Anopheles stephensi* larvae.

Some *B. laterosporus* strains show no apparent toxic activity to any test organism, and the observed toxicity is not homogeneous among toxic isolates (Favret and Yousten (1985) J. Invertebr. Pathol. 45:195-203, Rivers et al. (1991) J. Invertbr. Pathol. 58:444-447, and Singer (1996) Adv. Appl. Microbiol. 42:219-261). The results of the first bioassays with *B. laterosporus* demonstrated that some strains presented a larvicidal activity which was 1,000 times lower than that of the *B. thuringiensis* var. *israelensis* standard (Favret and Yousten (1985), Rivers et al. (1991)). These results discouraged the use of *B. laterosporus* in biological control. No entomocidal activity has been demonstrated against plant pathogens using isolates of *Brevibacillus* sp.

SUMMARY OF INVENTION

Compositions and methods for conferring insect resistance to bacteria, plants, plant cells, tissues and seeds are provided. Compositions include nucleic acid molecules encoding sequences for *Brevibacillus*-derived delta-endotoxin polypeptides, vectors comprising those nucleic acid molecules, and host cells comprising the vectors. Compositions also include the polypeptide sequences of the endotoxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules corresponding to delta-endotoxin nucleic acid sequences are provided. Additionally, amino acid sequences corresponding to the polynucleotides are encompassed. In particular, the present invention provides for an isolated nucleic acid molecule comprising a nucleotide sequence encoding the amino acid sequence shown in any of SEQ ID NO:2, 4, 7, or 10, or a nucleotide sequence set forth in any of SEQ ID NO:1, 3, 5, 6, 8, or 9, as well as variants and fragments thereof. Nucleotide sequences that are complementary to a nucleotide sequence of the invention, or that hybridize to a sequence of the invention are also encompassed.

The compositions and methods of the invention are useful for the production of organisms with resistance to plant pests, specifically bacteria and plants with resistance to these pests. These organisms and compositions derived from them are desirable for agricultural purposes. The compositions of the invention are also useful for generating altered or improved delta-endotoxin proteins that have pesticidal activity, or for detecting the presence of delta-endotoxin proteins or nucleic acids in products or organisms.

DETAILED DESCRIPTION

The present invention is drawn to compositions and methods for regulating insect resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess insecticidal activity. Thus, transformed bacteria, plants, plant cells, plant tissues and seeds are provided. Compositions are delta-endotoxin nucleic acids and proteins derived from a *Brevibacillus* organism. By "derived from" is intended that the nucleic acid or polypeptide is cloned or otherwise isolated from a *Brevibacillus* organism, or is a sequence that has been cloned or otherwise isolated from the *Brevibacillus* organism and subsequently altered (e.g., by making nucleotide and/or amino acid changes). The sequences find use in the construction of expression vectors for subsequent transformation into organisms of interest, as probes for the isolation of other delta-endotoxin genes, and for the generation of altered insecticidal proteins by methods known in the art, such as domain swapping or DNA shuffling. The proteins find use in controlling or killing lepidopteran, coleopteran, nematode, and other insect populations that are pathogenic to plants, and for producing compositions with insecticidal activity.

Exemplary *Brevibacillus* organisms from which the delta-endotoxin sequences encompassed by the present invention can be derived include *Brevibacillus agri, Brevibacillus borstelensis, Brevibacillus brevis, Brevibacillus centrosporus, Brevibacillus choshinensis, Brevibacillus formosus, Brevibacillus ginsengisoli, Brevibacillus invocatus, Brevibacillus laterosporus, Bacillus laterosporus, Brevibacillus levickii, Brevibacillus limnophilus, Brevibacillus parabrevis, Brevibacillus reuszeri, Brevibacillus* sp., and *Brevibacillus thermoruber*.

For the purposes of the present invention, a "*Brevibacillus*-derived delta-endotoxin" is intended a toxin from *Brevibacillus* sp. that has toxic activity against one or more pests, including, but not limited to, members of the Lepidoptera and Coleoptera orders, or a protein that has homology to such a protein. Delta-endotoxin proteins have been isolated from other organisms, including *Bacillus thuringiensis, Clostridium bifermentans* and *Paenibacillus popilliae*. However, prior to the present invention, these sequences were not known to exist in *Brevibacillus* organisms. Thus, the present invention provides a new source for identifying and isolating genes of agricultural significance.

Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having insecticidal activity. Processing may occur in the organism the protein is expressed in, or in the pest after ingestion of the protein.

Further encompassed herein are any delta-endotoxin sequence derived from a *Brevibacillus* organism. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," on the world wide web at biols.susx.ac.uk/Home/Neil_Crickmore/Bt/index.

Provided herein are novel isolated nucleotide sequences that confer pesticidal activity against plant-pathogenic pests. Also provided are the amino acid sequences of the delta-endotoxin proteins. The protein resulting from translation of this gene allows cells to control or kill insects that ingest it.

Isolated Nucleic Acid Molecules, and Variants and Fragments Thereof

One aspect of the invention pertains to isolated or recombinant nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid sequence (or DNA) is used herein to refer to a nucleic acid sequence (or DNA) that is no longer in its natural environment, for example in an in vitro or in a recombinant bacterial or plant host cell. In some embodiments, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include any delta-endotoxin derived from *Brevibacillus*. In various embodiments, the delta-endotoxin nucleotide sequence comprises the sequence set forth in SEQ ID NO:3, 6, or 9, and variants, fragments, and complements thereof. In some embodiments, the nucleotide sequence comprising SEQ ID NO:3, 6, or 9 is set forth in SEQ ID NO:1, 5, 8, 11, 12, 13, 14, or 15. In other embodiments, the variants and fragments of SEQ ID NO:3, 6, or 9 include the sequences corresponding to nucleotides 160-3819 of SEQ ID NO:1, nucleotides 4-1059 of SEQ ID NO:6, nucleotides 13-1059 of SEQ ID NO:6, nucleotides 151-1059 of SEQ ID NO:6, nucleotides 19-1893 of SEQ ID NO:9, nucleotides 46-1893 of SEQ ID NO:9, and nucleotides 52-1893 of SEQ ID NO:9, as well as variants and fragments of those sequences.

By "complement" is intended a nucleotide sequence that is sufficiently complementary to a given nucleotide sequence such that it can hybridize to the given nucleotide sequence to thereby form a stable duplex. The corresponding amino acid sequence for the delta-endotoxin protein encoded by this nucleotide sequence are set forth in SEQ ID NO:2, 4, 7, and 10.

Nucleic acid molecules that are fragments of these delta-endotoxin encoding nucleotide sequences are also encompassed by the present invention. By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below. Nucleic acid molecules that are fragments of a delta-endotoxin nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides, or up to the number of nucleotides present in a full-length delta-endotoxin encoding nucleotide sequence disclosed herein depending upon the intended use. By "contiguous" nucleotides is intended nucleotide residues that are immediately adjacent to one another. Fragments of the nucleotide sequences of the present invention will encode protein fragments that retain the biological activity of the delta-endotoxin protein and, hence, retain insecticidal activity. By "retains activity" is intended that the fragment will have at least about 30%, at least about 50%, at least about 70%, 80%, 90%, 95% or higher of the insecticidal activity of the delta-endotoxin protein. Methods for measuring insecticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100 contiguous amino acids, or up to the total number of amino acids present in a full-length delta-endotoxin protein of the invention.

Preferred delta-endotoxin proteins of the present invention are encoded by a nucleotide sequence sufficiently identical to any of the nucleotide sequences disclosed herein. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of one of SEQ ID NO:1-11). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin-like nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the delta-endotoxin encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining insecticidal activity. By "retains activity" is intended that the variant will have at least about 30%, at least about 50%, at least about 70%, or at least about 80% of the insecticidal activity of the native protein. Methods for measuring insecticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of the amino acid sequences of the present invention and known delta-endotoxin sequences. Examples of residues that are conserved but that may allow conservative amino acid substitutions and still retain activity include, for example, residues that have only conservative substitutions between all proteins contained in an alignment of the amino acid sequences of the present invention and known delta-endotoxin sequences. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer delta-endotoxin activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the delta-endotoxin nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known delta-endotoxin-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of delta-endotoxin encoding nucleotide sequence of the invention or a fragment or variant thereof. Methods for the preparation of probes for hybridization are generally known in the art and are disclosed in Sambrook and Russell, 2001, supra herein incorporated by reference.

For example, an entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in depending upon circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Delta-endotoxin proteins are also encompassed within the present invention. By "delta-endotoxin protein" is intended a protein having the amino acid sequence set forth in SEQ ID NO:2, 4, 7, or 10. Fragments, biologically active portions, and variants thereof are also provided, and may be used to practice the methods of the present invention. An "isolated protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in any of SEQ ID NO:2, 4, 7, or 10 and that exhibit insecticidal activity. A biologically active portion of a delta-endotoxin protein can be a polypeptide that is, for example, 10, 25, 50, 100 or more amino acids in length. Such biologically active portions can be prepared by recombinant techniques and evaluated for insecticidal activity. Methods for measuring insecticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2, 4, 7, or 10. In various embodiments, the fragments correspond to amino acids 54-1272 of SEQ ID NO:2, amino acids 21-651 of SEQ ID NO:4, amino acids 54-651 of SEQ ID NO:4, amino acids 2-352 of SEQ ID NO:7, amino acids 5-352 of SEQ ID NO:7, amino acids 51-352 of SEQ ID NO:7, amino acids 7-630 of SEQ ID NO:10, amino acids 16-630 of SEQ ID NO:10, amino acids 18-630 of SEQ ID NO:10, as well as variants and fragments thereof. The invention encompasses other fragments, however, such as any fragment in the protein greater than about 10, 20, 30, 50, 100, 150, 200, 250, 300, 350, 400, 400, 450, 500, 550, 600, 650, 700, 750, 800, 850, 900, 950, 1000, 1050, 1100, 1150, 1200, 1250, or 1300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:2, 4, 7, or 10. Variants also include polypeptides encoded by a nucleic acid molecule that hybridizes to the nucleic acid molecule of SEQ ID NO:1, 3, 5, 6, 8, 9, 11, 12, 13, 14, or 15, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining insecticidal activity. Methods for measuring insecticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of*

*Economic Entomology* 78:290-293; and U.S. Pat. No. 5,743, 477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of delta-endotoxin proteins that encode insecticidal activity. These delta-endotoxin proteins are encompassed in the present invention and may be used in the methods of the present invention. For example, the amino acid sequences corresponding to amino acids 54-1272 of SEQ ID NO:2, amino acids 21-651 of SEQ ID NO:4, amino acids 54-651 of SEQ ID NO:4, amino acids 2-352 of SEQ ID NO:7, amino acids 5-352 of SEQ ID NO:7, amino acids 51-352 of SEQ ID NO:7, amino acids 7-630 of SEQ ID NO:10, amino acids 16-630 of SEQ ID NO:10, amino acids 18-630 of SEQ ID NO:10, as well as variants and fragments thereof are encompassed herein. It will be understood that, when expressed in plants, it will be necessary to alter the alternate start codon to ATG for proper translation.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a delta-endotoxin may be altered by various methods, and that these alterations may result in DNA sequences encoding proteins with amino acid sequences different than that encoded by a delta-endotoxin of the present invention. This protein may be altered in various ways including amino acid substitutions, deletions, truncations, and insertions of one or more amino acids of SEQ ID NO:2, 4, 7, or 10, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Methods for such manipulations are generally known in the art. For example, amino acid sequence variants of a delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired insecticidal activity. However, it is understood that the ability of a delta-endotoxin to confer insecticidal activity may be improved by the use of such techniques upon the compositions of this invention. For example, one may express a delta-endotoxin in host cells that exhibit high rates of base misincorporation during DNA replication, such as XL-1 Red (Stratagene). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with insecticidal activity, for example by performing an assay to test for insecticidal activity. Generally, the protein is mixed and used in feeding assays. See, for example Marrone et al. (1985) *J. of Economic Entomology* 78:290-293. Such assays can include contacting plants with one or more insects and determining the plant's ability to survive and/or cause the death of the insects. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved insecticidal activity or target spectrum. Methods for generating recombinant proteins and testing them for insecticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A delta-endotoxin sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native, or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the delta-endotoxin is targeted to the chloroplast for expression. In this manner, where the delta-endotoxin is not directly inserted into the chloroplast, the expression cassette will additionally contain a nucleic acid encoding a transit peptide to direct the delta-endotoxin to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196: 1414-1421; and Shah et al. (1986) *Science* 233:478-481.

The delta-endotoxin gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell.

"Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The delta-endotoxin gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the delta-endotoxin are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, resolved in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the delta-endotoxin is then tested by hybridizing the filter to a radioactive probe derived from a delta-endotoxin, by methods known in the art (Sambrook and Russell, 2001, supra).

Western blot, biochemical assays and the like may be carried out on the transgenic plants to confirm the presence of protein encoded by the delta-endotoxin gene by standard procedures (Sambrook and Russell, 2001, supra) using antibodies that bind to one or more epitopes present on the delta-endotoxin protein.

Insecticidal Activity in Plants

In another aspect of the invention, one may generate transgenic plants expressing a delta-endotoxin that has insecticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for insecticidal activity.

Fertile plants expressing a delta-endotoxin may be tested for insecticidal activity, and the plants showing optimal activity selected for further breeding. Methods are available in the art to assay for insect activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, *macadamia*, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Insect Control

General methods for employing strains comprising a nucleotide sequence of the present invention, or a variant thereof, in insect control or in engineering other organisms as insecticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain an insecticidal gene and protein may be used for protecting agricultural crops and products from insects. In one aspect of the invention, whole, i.e., unlysed, cells of a toxin (insecticide)-producing organism are treated with reagents that prolong the activity of the toxin produced in the cell when the cell is applied to the environment of target insect(s).

Alternatively, the insecticide is produced by introducing a delta-endotoxin gene into a cellular host. Expression of the delta-endotoxin gene results, directly or indirectly, in the intracellular production and maintenance of the insecticide. In one aspect of this invention, these cells are then treated under conditions that prolong the activity of the toxin produced in the cell when the cell is applied to the environment of target insect(s). The resulting product retains the toxicity of the toxin. These naturally encapsulated insecticides may then be formulated in accordance with conventional techniques for application to the environment hosting a target insect, e.g., soil, water, and foliage of plants. See, for example EPA 0192319, and the references cited therein. Alternatively, one may formulate the cells expressing a gene of this invention such as to allow application of the resulting material as a insecticide.

Insecticidal Compositions

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, insecticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the insecticidal formulation.

Methods of applying an active ingredient of the present invention or an agrochemical composition of the present invention that contains at least one of the insecticidal proteins produced by the bacterial strains of the present invention include leaf application, seed coating and soil application. The number of applications and the rate of application depend on the intensity of infestation by the corresponding insect.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such insecticidal polypeptide, the polypeptide may be present in a concentration of from about 1% to about 99% by weight.

Lepidopteran, coleopteran, or other insects may be killed or reduced in numbers in a given area by the methods of the invention, or may be prophylactically applied to an environmental area to prevent infestation by a susceptible insect. Preferably the insect ingests, or is contacted with, a insecticidally-effective amount of the polypeptide. By "insecticidally-effective amount" is intended an amount of the insecticide that is able to bring about death to at least one insect, or to noticeably reduce insect growth, feeding, or normal physiological development. This amount will vary depending on such factors as, for example, the specific target insects to be controlled, the specific environment, location, plant, crop, or agricultural site to be treated, the environmental conditions, and the method, rate, concentration, stability, and quantity of application of the insecticidally-effective polypeptide composition. The formulations may also vary with respect to climatic conditions, environmental considerations, and/or frequency of application and/or severity of insect infestation.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera. In various embodiments, the pest does not include Dipteran pests.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrimidae. Superfamily Hydrophiloidea includes the family Hydrophilidae. Superfamily Staphylinoidea includes the families Silphidae and Staphylimidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachimidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, Crambidae, and Tineidae.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Methods for Increasing Plant Yield

Methods for increasing plant yield are provided. The methods comprise introducing into a plant or plant cell a polynucleotide comprising an insecticidal sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the insecticidal sequence.

In specific methods, plant yield is increased as a result of improved insect resistance of a plant expressing an insecticidal protein disclosed herein. Expression of the insecticidal protein results in a reduced ability of an insect to infest or feed on the plant, thus improving plant yield.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides:
Carbofuran, Organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

The following examples are offered by way of illustration and not by way of limitation.

EXPERIMENTAL

Example 1

Identification of Axmi-134 from *Brevibacillus* Strain ATX15530

The complete gene sequence was identified as follows:
Preparation of extrachromosomal DNA from the strain. Extrachromosomal DNA contains a mixture of some or all of the following: plasmids of various size; phage chromosomes; genomic DNA fragments not separated by the purification protocol; other uncharacterized extrachromosomal molecules.

Mechanical or enzymatic shearing of the extrachromosomal DNA to generate size-distributed fragments.

Sequencing of the fragmented DNA by high-throughput pyrosequencing methods. Identification of putative toxin genes via homology and/or other computational analyses.

When required, sequence finishing of the gene of interest by one of several PCR or cloning strategies (e.g. TAIL-PCR). The sequence of the axmi-134 open reading frame is provided herein as SEQ ID NO:1 and encodes the AXMI-134 protein (SEQ ID NO: 2. Comparison of AXMI-134 vs protein databases identified the following homologies:

Known homologs and approximate percent identity:

Cry43Aa1—60%

Cry43Aa1—60%

Cry43Ba1—55%

Example 2

Heterologous Expression of AXMI-134

The complete ORF of axmi-134 (3.82 kb which encodes 1272 amino acid long protein) was amplified from *Brevibacillus* strain ATX15530 using appropriate primers. It was cloned into an *E. coli* expression vector based on pRSF1b (to give pAX5479) and a *Bacillus* vector based on pAX916 (to give pAX5481). The resulting clones were confirmed by restriction analysis and finally, by complete sequencing of the cloned gene. For expression in *E. coli*, BL21*DE3 was transformed with pAX5479. Single colony was inoculated in LB supplemented with kanamycin and grown overnight at 37° C. The following day, fresh medium was inoculated in duplicate with 1% of overnight culture and grown at 37° C. to logarithmic phase. Subsequently, cultures were induced with 1 mM IPTG for 3 hours at 37° C. or overnight at 20° C. Each cell pellet was suspended in 50 mM sodium carbonate buffer, pH 10.5 supplemented with 1 mM DTT and sonicated. Analysis by SDS-PAGE detected expression of a 144 kD protein corresponding to Axmi134. For expression in *Bacillus*, a laboratory strain of *Bacillus* was transformed with pAX5481 and a single colony was grown in CYS-glu medium for 3 days to sporulation. Cell pellet was then extracted with 50 mM sodium carbonate buffer, pH 10.5 supplemented with 1 mM DTT. Soluble fraction showed presence of a ~144 kD Axmi134 protein. Trypsinization of Axmi134 cleaved the full length protein, resulting in two protein fragments of about 85 kDa and 65 kDa.

Example 3

Pesticidal Activity of AXMI-134

Soluble extracts containing Axmi134 were tested separately in insect assays with appropriate controls at an approximate concentration of 200 ng/ul. In this assay, a 5 day read of the plates showed AXMI-134 to have pesticidal activity on diamondback moth (DBM) and Colorado potato beetle (CPB) (see Table 2 below). Trypsin treatment of AXMI-134 resulted in strong mortality and stunting on DBM and CPB, (Table 2) respectively. Table 1 shows a description of the scoring assignments used herein

TABLE 1

Description of Scoring System

| Score | Description |
|---|---|
| 0 | no effect observed |
| 1 | mild non-uniform stunting |
| 2 | moderate non-uniform stunting |
| 3 | moderate to severe uniform stunting |
| 4 | mortality (<100%) with uniform stunting |
| 5 | complete mortality |

TABLE 2

Activity of AXMI134 on Diamondback moth (*Plutella xylostella*) and Colorado potato beetle (*Leptinotarsa decemlineata*).

| Pest | AXMI134 | AXMI134 (Trypsin treated) |
|---|---|---|
| Diamondback Moth | 4 - Uniform stunt, 60% mortality | 4 - Uniform stunt, 80% mortality |
| Colorado Potato Beetle | 3 - Light feeding on leaf disks, 100% mortality | 5 - Little or no feeding on leaf disks, 100% mortality |

Example 4

N-Terminal Deletions of AXMI-134

A series of N-terminal deletions of AXMI-134 were planned and performed using PCR-based cloning. The deletion mutants thus generated were cloned and expressed, and resulting protein products were tested for activity against selected agricultural pests. An 'ATG' start codon, encoding methionine (M), was added at the beginning of each variant. Listed here are the start sites of the deletion variants and their starting amino acid sequences (corresponding to SEQ ID NO:2).

TABLE 3

Location of Protein start sites in N-terminal Deletions

| Deletion | Starting position Relative to SEQ ID NO:2 |
|---|---|
| D3 | 21 |
| D5 | 39 |
| D6 | 55 |
| D7 | 63 |
| D8 | 73 |
| D9 | 83 |
| D11 | 103 |
| D12 | 119 |

All deletion mutants were PCR amplified from construct pAX5481 (which contains the full-length axmi-134 gene) and cloned into the BamHI site in the expression vector pAX916. All constructs were transformed into host cells and grown to measure the expression of the truncated variants. Soluble protein was extracted in 50 mM sodium carbonate buffer, pH 10.5. Whole culture (W) and soluble (S) fractions were analyzed by SDS-PAGE.

Deletions at the N-terminus had differing effects on the solubility of AXMI-134. Variant D3, cloned into pAX4245 and starting at position 21 of the native AXMI-134 amino acid sequence, showed enhanced solubility as estimated by PAGE analysis. Variants D5, D6, D7, D8, D9, and D12 expressed poorly and produced little or no soluble protein under the conditions tested. Variant D11 expressed and produced soluble protein at levels comparable to the wild-type AXMI-134 protein.

Soluble fractions were assayed at three concentrations (100, 50, and 10 ng per microliter) against Colorado Potato Beetle (CPB) using leaf-dip assays. Results are presented in Table 3. Scores are presented as means of 3 replicate experiments, with individual component scores presented parenthetically. The scoring key for Table 4 is the same as for Table 1 above.

Variant D3 (cloned into pAX4245) showed enhanced activity versus the wild-type against CPB in replicate assays. The LC50 for variant D3 was found to be 52.5 ng/ml and the LC50 for the wild-type was found to be 800 ng/ml for CPB. The remaining variants showed no activity in this assay.

TABLE 4

Activity of Axmi134 variants against Colorado Potato Beetle

| Form of Axmi134 | 100 ng/ul | 50 ng/ul | 10 ng/ul |
|---|---|---|---|
| Full length (pAX5481) | 2.33(2,2,3) | 2.67(2,3,3) | 0 |
| Deleted form D3 (pAX4245) | 4.67(5,4,5) | 3.67(3,4,4) | 2(2,2,2) |

N-terminal deletions may be of general utility in designing active variants of Cry-type delta endotoxins. The N-terminal portion of AXMI-134 contained multiple asparagine (N) and glutamine (Q) residues. Other Cry-type proteins have sequences near the N terminus that contain similar polar residues. Removal of this portion of the protein may facilitate toxin activation.

Example 5

Identification of Axmi-159 from *Brevibacillus* Strain ATX15530

The complete gene sequence was identified as follows:
Preparation of extrachromosomal DNA from the strain. Extrachromosomal DNA contains a mixture of some or all of the following: plasmids of various size; phage chromosomes; genomic DNA fragments not separated by the purification protocol; other uncharacterized extrachromosomal molecules.

Mechanical or enzymatic shearing of the extrachromosomal DNA to generate size-distributed fragments.

Sequencing of the fragmented DNA by high-throughput pyrosequencing methods. Identification of putative toxin genes via homology and/or other computational analyses.

When required, sequence finishing of the gene of interest by one of several PCR or cloning strategies (e.g. TAIL-PCR).

The sequence of the axmi-159 open reading frame is provided herein as SEQ ID NO:6 and encodes the AXMI-159 protein (SEQ ID NO:7). Comparison of AXMI-159 vs protein databases identified the following homologies:
AXMI-159 homologs and approximate percent identity:
Axmi012—24.0%
Cry35Ba1—21.1%
Cry35Ac1—20.5%

Example 6

Identification of Axmi-160 from *Brevibacillus* Strain ATX15530

The complete gene sequence was identified as follows:
Preparation of extrachromosomal DNA from the strain. Extrachromosomal DNA contains a mixture of some or all of the following: plasmids of various size; phage chromosomes; genomic DNA fragments not separated by the purification protocol; other uncharacterized extrachromosomal molecules.

Mechanical or enzymatic shearing of the extrachromosomal DNA to generate size-distributed fragments.

Sequencing of the fragmented DNA by high-throughput pyrosequencing methods. Identification of putative toxin genes via homology and/or other computational analyses.

When required, sequence finishing of the gene of interest by one of several PCR or cloning strategies (e.g. TAIL-PCR).

The sequence of the axmi-160 open reading frame is provided herein as SEQ ID NO:9 and encodes the AXMI-160 protein (SEQ ID NO:10). Comparison of AXMI-160 vs protein databases identified the following homologies:
Known homologs and approximate percent identity:
lethal factor—20.5%
Vip2Ba1—20.7%

Example 7

Synthetic Genes

Alternate DNA sequences encoding the proteins of the invention were developed. They are provided as follows:

| Encoded Protein | SEQ ID NO of Synthetic Gene | Corresponding amino acid encoded |
|---|---|---|
| AXMI-134(v01) | 12 | amino acids 1-677 of SEQ ID NO:2 |
| AXMI-134(v02) | 13 | amino acids 21-662 of SEQ ID NO:2 with N-terminal methionine addition |
| AXMI-159 | 14 | amino acids 1-352 of SEQ ID NO:7 |
| AXMI-160 | 15 | amino acids 1-630 of SEQ ID NO:10 |

Example 8

Additional Assays for Pesticidal Activity

The ability of an insecticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be in a liquid, solid, or slurry form. The material to be tested may be placed upon the surface and then allowed to dry or incorporate into the diet. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays with arthropods*. CRC, Boca Raton, Fla. Alternatively, assays are commonly described in the journals "Arthropod Management Tests" and "Journal of Economic Entomology" or by discussion with members of the Entomological Society of America (ESA).

Example 9

Vectoring of the Insecticidal Genes of the Invention for Plant Expression

Each of the coding regions of the genes of the invention is connected independently with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

Example 10

Transformation of the Genes of the Invention into Plant Cells by *Agrobacterium*-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

Example 11

Transformation of Maize Cells with the Insecticidal Genes of the Invention

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/mL Stock) 2,4-D), and incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240,842).

DNA constructs designed to express the genes of the invention in plant cells are accelerated into plant tissue using an aerosol beam accelerator, using conditions essentially as described in PCT Publication No. WO/0138514. After beaming, embryos are incubated for 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | per liter | Source |
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |

-continued

| DN62A5S Media | | |
|---|---|---|
| Components | per liter | Source |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/1 of a 5 mg/ml stock solution of Silver Nitrate (Phytotechnology Labs). This recipe yields about 20 plates.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated or recombinant nucleic acid molecule comprising a nucleotide sequence selected from the group consisting of:
 a) the nucleotide sequence of SEQ ID NO:1 or 5, or the full-length complement thereof;
 b) a nucleotide sequence that encodes a polypeptide comprising the amino acid sequence of SEQ ID NO:4; and
 c) a nucleotide sequence that encodes a polypeptide comprising an amino acid sequence having at least 95% sequence identity to the amino acid sequence of SEQ ID NO:4, wherein said polypeptide has pesticidal activity against a plant pest;
 and wherein said nucleotide sequence is operably linked to a heterologous promoter.

2. The recombinant nucleic acid molecule of claim 1, wherein said nucleotide sequence is a synthetic sequence that has been designed for expression in a plant.

3. The recombinant nucleic acid of claim 2, wherein said nucleic acid sequence is SEQ ID NO:12.

4. A vector comprising the nucleic acid molecule of claim 1.

5. The vector of claim 4, further comprising a nucleic acid molecule encoding a heterologous polypeptide.

6. A host cell that contains the nucleic acid molecule of claim 1.

7. The host cell of claim 6, wherein said host cell is a bacterial host cell.

8. The host cell of claim 6, wherein said host cell is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the nucleic acid molecule of claim 1.

12. An isolated polypeptide with insecticidal activity, selected from the group consisting of:
 a) a polypeptide comprising the amino acid sequence of SEQ ID NO:4;
 b) a polypeptide that is encoded by the nucleotide sequence of SEQ ID NO:1, 3, or 5;
 c) a polypeptide that is at least 95% sequence identity to the amino acid sequence of SEQ ID NO:4, wherein said polypeptide has pesticidal activity against a plant pest;
 and wherein said polypeptide is operably linked to a leader sequence, a signal sequence or a transit peptide.

13. A composition comprising the polypeptide of claim 12.

14. The composition of claim 13, wherein said composition is selected from the group consisting of a powder, dust, pellet, granule, spray, emulsion, colloid, and solution.

15. The composition of claim 13, wherein said composition is prepared by desiccation, lyophilization, homogenization, extraction, filtration, centrifugation, sedimentation, or concentration of a culture of Bacillus thuringiensis cells.

16. The composition of claim 14, comprising from about 1% to about 99% by weight of said polypeptide.

17. A method for controlling or killing a plant pest population comprising contacting said population with an insecticidally-effective amount of a polypeptide, wherein said polypeptide is selected from the group consisting of:
 a) a polypeptide comprising the amino acid sequence of SEQ ID NO:4;
 b) a polypeptide that is encoded by the nucleotide sequence of SEQ ID NO:1, 3, or 5;
 c) a polypeptide that is at least 95% sequence identity to the amino acid sequence of SEQ ID NO:4, wherein said polypeptide has pesticidal activity against a plant pest.

18. A method for producing a polypeptide with insecticidal activity, comprising culturing the host cell of claim 6 under conditions in which the nucleic acid molecule encoding the polypeptide is expressed.

19. A plant or a plant cell having stably incorporated into its genome a DNA construct comprising a nucleotide sequence that encodes a protein having insecticidal activity, wherein said nucleotide sequence is selected from the group consisting of:
 a) the nucleotide sequence of SEQ ID NO:1 or 5;
 b) a nucleotide sequence that encodes a polypeptide comprising the amino acid sequence of SEQ ID NO:4; and
 c) a nucleotide sequence that encodes a polypeptide comprising an amino acid sequence having at least 95% sequence identity to the amino acid sequence of SEQ ID NO:4, wherein said polypeptide has pesticidal activity against a plant pest;
 wherein said nucleotide sequence is operably linked to a promoter that drives expression of a coding sequence in a plant cell.

20. A method for protecting a plant from an insect pest, comprising introducing into said plant or cell thereof at least one expression vector comprising a nucleotide sequence that encodes a insecticidal polypeptide, wherein said nucleotide sequence is selected from the group consisting of:
- a) the nucleotide sequence of SEQ ID NO:1 or 5;
- b) a nucleotide sequence that encodes a polypeptide comprising the amino acid sequence of SEQ ID NO:4; and
- c) a nucleotide sequence that encodes a polypeptide comprising an amino acid sequence having at least 95% sequence identity to the amino acid sequence of SEQ ID NO:4, wherein said polypeptide has pesticidal activity against a plant pest; and wherein said nucleotide sequence is operably linked to a promoter that drives expression of a coding sequence in a plant cell.

21. The isolated or recombinant nucleic acid of claim 1, wherein said promoter is capable of driving expression of said nucleotide sequence in a plant cell.

* * * * *

SEQUENCE LISTING

```
<160> NUMBER OF SEQ ID NOS: 15

<210> SEQ ID NO 1
<211> LENGTH: 3819
<212> TYPE: DNA
<213> ORGANISM: Brevibacillus
<220> FEATURE:
<221> NAME/KEY: CDS
<222> LOCATION: (1)...(3819)

<400> SEQUENCE: 1 atg aat caa aat caa aat cag aat cag aat caa aat aaa aat gaa ctt        48
Met Asn Gln Asn Gln Asn Gln Asn Gln Asn Gln Asn Lys Asn Glu Leu
 1               5                  10                  15 caa atc ata gaa cct tca agc gat tct ttt ctt tat agt cac aac aat        96
Gln Ile Ile Glu Pro Ser Ser Asp Ser Phe Leu Tyr Ser His Asn Asn
             20                  25                  30 tat ccg tat tcc act gat cca aat aca gta tta cac ggt agg aat tac       144
Tyr Pro Tyr Ser Thr Asp Pro Asn Thr Val Leu His Gly Arg Asn Tyr
         35                  40                  45 aaa gag tgg cta aac atg tgt aca ggt aca gac gat tca cga ggt ccc       192
Lys Glu Trp Leu Asn Met Cys Thr Gly Thr Asp Asp Ser Arg Gly Pro
     50                  55                  60 gaa gct gct tct act gca aga tca gct ata tcg gtt gcg att act ata       240
Glu Ala Ala Ser Thr Ala Arg Ser Ala Ile Ser Val Ala Ile Thr Ile
 65                  70                  75                  80 agc acc aca att ctt ggc tta cta ggt gtt ccg ttt gca tct cag atc       288
Ser Thr Thr Ile Leu Gly Leu Leu Gly Val Pro Phe Ala Ser Gln Ile
                 85                  90                  95 ggg gca ttt tat aac ttc gta ttg aat acg gta tgg cct cag gga aat       336
Gly Ala Phe Tyr Asn Phe Val Leu Asn Thr Val Trp Pro Gln Gly Asn
            100                 105                 110 aac caa tgg gaa gag ttc atg aga cat gta gaa aat ctc ata aac gaa       384
Asn Gln Trp Glu Glu Phe Met Arg His Val Glu Asn Leu Ile Asn Glu
        115                 120                 125 cga ata gct gat tat gca aga agt aag gca ctt gca gaa tta acg ggt       432
Arg Ile Ala Asp Tyr Ala Arg Ser Lys Ala Leu Ala Glu Leu Thr Gly
    130                 135                 140 tta ggt aat aac tta aat tta tat aga gag gct ttt gaa gat tgg aga       480
Leu Gly Asn Asn Leu Asn Leu Tyr Arg Glu Ala Phe Glu Asp Trp Arg
145                 150                 155                 160 cga aat cct act agt caa gaa gct aaa acc cgc gta ata gat aga ttc       528
Arg Asn Pro Thr Ser Gln Glu Ala Lys Thr Arg Val Ile Asp Arg Phe
                165                 170                 175 cgt ata cta gat ggc tta ttt gaa gca tat atg cca tca ttt gca gta       576
Arg Ile Leu Asp Gly Leu Phe Glu Ala Tyr Met Pro Ser Phe Ala Val
            180                 185                 190
```

-continued

| | | |
|---|---|---|
| caa ggt ttt gaa gta caa tta tta aca gtg tat gca tcc gct gca aat<br>Gln Gly Phe Glu Val Gln Leu Leu Thr Val Tyr Ala Ser Ala Ala Asn<br>      195                    200                  205 | 624 |
| atc cat tta ttt tta tta aga gat agc tct att tac ggt ttg gat tgg<br>Ile His Leu Phe Leu Leu Arg Asp Ser Ser Ile Tyr Gly Leu Asp Trp<br>210                    215                    220 | 672 |
| gga tta agt caa act aat gtt aac gaa aat tac aat cgc caa ata agg<br>Gly Leu Ser Gln Thr Asn Val Asn Glu Asn Tyr Asn Arg Gln Ile Arg<br>225                  230                  235                  240 | 720 |
| cac acc gca acg tat gca aat cat tgt aca act tgg tat caa act ggt<br>His Thr Ala Thr Tyr Ala Asn His Cys Thr Thr Trp Tyr Gln Thr Gly<br>              245                  250                  255 | 768 |
| tta caa aga ttg caa ggt acc aat gct acc agt tgg ggc gct tat aat<br>Leu Gln Arg Leu Gln Gly Thr Asn Ala Thr Ser Trp Gly Ala Tyr Asn<br>          260                  265                  270 | 816 |
| aga ttt aga agg gaa atg acg tta aca gta tta gat att agt tca tta<br>Arg Phe Arg Arg Glu Met Thr Leu Thr Val Leu Asp Ile Ser Ser Leu<br>275                    280                    285 | 864 |
| ttt tca aat tat gat tat cgt agt tat cca aca gag gta agg gga gag<br>Phe Ser Asn Tyr Asp Tyr Arg Ser Tyr Pro Thr Glu Val Arg Gly Glu<br>          290                  295                  300 | 912 |
| ctt acg aga gaa att tat acg gat cca gta ggc ttt ggc tgg cag aat<br>Leu Thr Arg Glu Ile Tyr Thr Asp Pro Val Gly Phe Gly Trp Gln Asn<br>305                    310                  315                  320 | 960 |
| aat gca cca tca ttc gct gaa ata gaa aat cta gca att agg gca cca<br>Asn Ala Pro Ser Phe Ala Glu Ile Glu Asn Leu Ala Ile Arg Ala Pro<br>              325                  330                  335 | 1008 |
| aga acc gtt act tgg tta aat tca aca aga att cat aca ggg acc ttg<br>Arg Thr Val Thr Trp Leu Asn Ser Thr Arg Ile His Thr Gly Thr Leu<br>          340                  345                  350 | 1056 |
| cag ggc tgg agt ggt tct aac aga tat tgg gca gct cac atg caa aac<br>Gln Gly Trp Ser Gly Ser Asn Arg Tyr Trp Ala Ala His Met Gln Asn<br>355                    360                  365 | 1104 |
| ttt tca gaa acc aat tca gga aat ata aga ttt gac ggt cct ctc tat<br>Phe Ser Glu Thr Asn Ser Gly Asn Ile Arg Phe Asp Gly Pro Leu Tyr<br>          370                  375                  380 | 1152 |
| ggg tcg acg gta ggt act att att cgt act gat aat tac gaa atg ggg<br>Gly Ser Thr Val Gly Thr Ile Ile Arg Thr Asp Asn Tyr Glu Met Gly<br>385                    390                  395                  400 | 1200 |
| aac cga gat att tac acc att act tca gaa gct gtt ggc gcc ctt tgg<br>Asn Arg Asp Ile Tyr Thr Ile Thr Ser Glu Ala Val Gly Ala Leu Trp<br>              405                  410                  415 | 1248 |
| cca cat ggt caa act gtg ttg gga gtc gct tcg gct aga ttt act tta<br>Pro His Gly Gln Thr Val Leu Gly Val Ala Ser Ala Arg Phe Thr Leu<br>          420                  425                  430 | 1296 |
| aga cat ctt tcc aat aat ttt aca cag gtg ctg gtg tat gag aat cca<br>Arg His Leu Ser Asn Asn Phe Thr Gln Val Leu Val Tyr Glu Asn Pro<br>435                    440                  445 | 1344 |
| ata agt aat agt ttt aat aga tca act gta act agt gaa tta cct gga<br>Ile Ser Asn Ser Phe Asn Arg Ser Thr Val Thr Ser Glu Leu Pro Gly<br>          450                  455                  460 | 1392 |
| gaa aac tca gat agg cca act gat agc gat tat agt cat aga cta acg<br>Glu Asn Ser Asp Arg Pro Thr Asp Ser Asp Tyr Ser His Arg Leu Thr<br>465                    470                  475                  480 | 1440 |
| tgt atc aca gct ttt cga gct gga aat aat ggt acg gtt cca gta ttt<br>Cys Ile Thr Ala Phe Arg Ala Gly Asn Asn Gly Thr Val Pro Val Phe<br>              485                  490                  495 | 1488 |
| ggc tgg aca tct aga act gtt aat cgc gac aat ata att gag caa aac<br>Gly Trp Thr Ser Arg Thr Val Asn Arg Asp Asn Ile Ile Glu Gln Asn | 1536 |

-continued

```
                500                      505                       510
aaa att aca caa ttc cca ggt gtt aag tca cac act ctc aac aat tgt       1584
Lys Ile Thr Gln Phe Pro Gly Val Lys Ser His Thr Leu Asn Asn Cys
            515                 520                 525 caa gta gtt aga ggg act gga ttt act gga gga gac tgg ttg aga cca       1632
Gln Val Val Arg Gly Thr Gly Phe Thr Gly Gly Asp Trp Leu Arg Pro
530                 535                 540 aat aat aat ggt aca ttt aga cta act att act tca ttc tcg agc caa       1680
Asn Asn Asn Gly Thr Phe Arg Leu Thr Ile Thr Ser Phe Ser Ser Gln
545                 550                 555                 560 tct tac cga atc cgc tta cgt tat gct act tca gta ggg aat act tct       1728
Ser Tyr Arg Ile Arg Leu Arg Tyr Ala Thr Ser Val Gly Asn Thr Ser
                565                 570                 575 tta gtt ata tct tct tct gat gca ggt att tct tcc aca aca att ccg       1776
Leu Val Ile Ser Ser Ser Asp Ala Gly Ile Ser Ser Thr Thr Ile Pro
            580                 585                 590 ctt act tca aca ata aca tca ctg ccc caa act gta cca tac cag gct       1824
Leu Thr Ser Thr Ile Thr Ser Leu Pro Gln Thr Val Pro Tyr Gln Ala
        595                 600                 605 ttt agg gtt gta gat tta cct att act ttt aca aca cct act acc caa       1872
Phe Arg Val Val Asp Leu Pro Ile Thr Phe Thr Thr Pro Thr Thr Gln
610                 615                 620 aga aat tat acg ttt gat ttc cgt ctc caa aat cca tct aac gca aat       1920
Arg Asn Tyr Thr Phe Asp Phe Arg Leu Gln Asn Pro Ser Asn Ala Asn
625                 630                 635                 640 gta ttc att gat aga ttt gaa ttt gtt cca att ggg ggt tct ttg tct       1968
Val Phe Ile Asp Arg Phe Glu Phe Val Pro Ile Gly Gly Ser Leu Ser
                645                 650                 655 gag tat gaa acc aaa cat cag cta gaa aaa gca agg aaa gcg gtg aac       2016
Glu Tyr Glu Thr Lys His Gln Leu Glu Lys Ala Arg Lys Ala Val Asn
            660                 665                 670 gat ttg ttt acc aat gaa tcg aaa aat gtg tta aaa aaa gaa act act       2064
Asp Leu Phe Thr Asn Glu Ser Lys Asn Val Leu Lys Lys Glu Thr Thr
        675                 680                 685 gat tat gac ata gat caa gca gca aac ttg gta gaa tgt ata tca gat       2112
Asp Tyr Asp Ile Asp Gln Ala Ala Asn Leu Val Glu Cys Ile Ser Asp
690                 695                 700 gaa tgt gca aat gca aaa atg atc cta tta gat gaa gta aaa tat gcg       2160
Glu Cys Ala Asn Ala Lys Met Ile Leu Leu Asp Glu Val Lys Tyr Ala
705                 710                 715                 720 aaa caa ctc agc gaa gcc cgc aat cta ctt cta aat ggt aat ttt gaa       2208
Lys Gln Leu Ser Glu Ala Arg Asn Leu Leu Leu Asn Gly Asn Phe Glu
                725                 730                 735 tac caa gat aga gat ggg gag aat cca tgg aaa aca agt ccc aat gtt       2256
Tyr Gln Asp Arg Asp Gly Glu Asn Pro Trp Lys Thr Ser Pro Asn Val
            740                 745                 750 acc atc caa gag aat aat ccc att ttt aaa ggc cgt tat ctc agt atg       2304
Thr Ile Gln Glu Asn Asn Pro Ile Phe Lys Gly Arg Tyr Leu Ser Met
        755                 760                 765 tcg ggt gcg aac aat atc gag gta aca aat gat ata ttc ccc act tat       2352
Ser Gly Ala Asn Asn Ile Glu Val Thr Asn Asp Ile Phe Pro Thr Tyr
770                 775                 780 gca tac caa aaa att gat gaa tcc aaa tta aaa ccc tat acg cgt tat       2400
Ala Tyr Gln Lys Ile Asp Glu Ser Lys Leu Lys Pro Tyr Thr Arg Tyr
785                 790                 795                 800 aaa gtt cga ggg ttt gtt gga aat agt aaa gat tta gag ttg ttg att       2448
Lys Val Arg Gly Phe Val Gly Asn Ser Lys Asp Leu Glu Leu Leu Ile
                805                 810                 815 aca cga tat aat gaa gaa gta gat gcg att tta aat gta gca aat gat       2496
Thr Arg Tyr Asn Glu Glu Val Asp Ala Ile Leu Asn Val Ala Asn Asp
```

```
                Thr Arg Tyr Asn Glu Glu Val Asp Ala Ile Leu Asn Val Ala Asn Asp
                            820                 825                 830 ata cca cat gct ccg aca cct ttc tgc ggt gga ttt gat cga tgc aag       2544
Ile Pro His Ala Pro Thr Pro Phe Cys Gly Gly Phe Asp Arg Cys Lys
            835                 840                 845 cca cat tct tat cct cct atg aat cca gaa tgt cac cat gat gta ata       2592
Pro His Ser Tyr Pro Pro Met Asn Pro Glu Cys His His Asp Val Ile
    850                 855                 860 aat aac att gaa ata tcc tct cct tgc cat cac aat aag atg gtt gat       2640
Asn Asn Ile Glu Ile Ser Ser Pro Cys His His Asn Lys Met Val Asp
865                 870                 875                 880 aac gct gat aca tct tct cgc cat agt gaa tta ggt aaa aaa cat ggc       2688
Asn Ala Asp Thr Ser Ser Arg His Ser Glu Leu Gly Lys Lys His Gly
                885                 890                 895 att tgt cat gaa tct cat cat ttt gaa ttc cat att gat aca gga aaa       2736
Ile Cys His Glu Ser His His Phe Glu Phe His Ile Asp Thr Gly Lys
            900                 905                 910 atc gat ttg gtc gaa aat ttg gga att tgg gtt ata ttt aaa ata tgt       2784
Ile Asp Leu Val Glu Asn Leu Gly Ile Trp Val Ile Phe Lys Ile Cys
    915                 920                 925 tcc aca gat ggt tac gca aca tta gat aat ttg gaa gtt att gaa gag       2832
Ser Thr Asp Gly Tyr Ala Thr Leu Asp Asn Leu Glu Val Ile Glu Glu
930                 935                 940 ggt cct tta gga gcc gaa tca tta gaa cgt gtg aaa aga aga gaa aag       2880
Gly Pro Leu Gly Ala Glu Ser Leu Glu Arg Val Lys Arg Arg Glu Lys
945                 950                 955                 960 aaa tgg aaa cat cac atg gaa cac aag tgt tca gaa act aaa cat gta       2928
Lys Trp Lys His His Met Glu His Lys Cys Ser Glu Thr Lys His Val
                965                 970                 975 tac cat gct gcg aaa caa gcg gtg gtg gcg tta ttc aca aac act caa       2976
Tyr His Ala Ala Lys Gln Ala Val Val Ala Leu Phe Thr Asn Thr Gln
            980                 985                 990 tat gat aga ttg aag ttc gaa aca acc ata tcc aat att cta ttt gct       3024
Tyr Asp Arg Leu Lys Phe Glu Thr Thr Ile Ser Asn Ile Leu Phe Ala
    995                 1000                1005 gat tat ctc gtg tcg tca att ccg ttt gta tat aat aaa tgg tta cca       3072
Asp Tyr Leu Val Ser Ser Ile Pro Phe Val Tyr Asn Lys Trp Leu Pro
    1010                1015                1020 gat gtt cca ggt atg aat tat gat atc tat aca gaa tta aaa aat ctg       3120
Asp Val Pro Gly Met Asn Tyr Asp Ile Tyr Thr Glu Leu Lys Asn Leu
1025                1030                1035                1040 att acg gga gct ttc aat cta tac gat caa cga aat att ata aaa aat       3168
Ile Thr Gly Ala Phe Asn Leu Tyr Asp Gln Arg Asn Ile Ile Lys Asn
                1045                1050                1055 gga gac ttt aat aac gga ctc atg cat tgg cat gca aca cct cat gcg       3216
Gly Asp Phe Asn Asn Gly Leu Met His Trp His Ala Thr Pro His Ala
            1060                1065                1070 aga gta gag caa ata gat aat agg tct gtg ctg gtg ctt cca aat tat       3264
Arg Val Glu Gln Ile Asp Asn Arg Ser Val Leu Val Leu Pro Asn Tyr
    1075                1080                1085 gct gcc aat gtt tca caa gag gtt tgt tta gaa cac aat cgt ggt tat       3312
Ala Ala Asn Val Ser Gln Glu Val Cys Leu Glu His Asn Arg Gly Tyr
    1090                1095                1100 gta tta cgt gta acg gcg aaa aaa gaa ggt cct gga att gga tat gtt       3360
Val Leu Arg Val Thr Ala Lys Lys Glu Gly Pro Gly Ile Gly Tyr Val
1105                1110                1115                1120 acg ttc agt gat tgt gca aat aat ata gaa aaa ctg aca ttt act tct       3408
Thr Phe Ser Asp Cys Ala Asn Asn Ile Glu Lys Leu Thr Phe Thr Ser
                1125                1130                1135
```

| | |
|---|---|
| tgc gat tat ggt aca aac gaa gtg cca tat gag caa tct aat tat cct<br>Cys Asp Tyr Gly Thr Asn Glu Val Pro Tyr Glu Gln Ser Asn Tyr Pro<br>             1140               1145               1150 | 3456 |
| aca gac gga gtt tca tac gga caa cat ggt tgt aat ata gac aga gta<br>Thr Asp Gly Val Ser Tyr Gly Gln His Gly Cys Asn Ile Asp Arg Val<br>1155               1160               1165 | 3504 |
| ccg tac gaa caa tct ggt tat cct aca gac gga gta tcg tac gaa caa<br>Pro Tyr Glu Gln Ser Gly Tyr Pro Thr Asp Gly Val Ser Tyr Glu Gln<br>             1170               1175               1180 | 3552 |
| tct ggt tat cgt aca gac gga gta ctg tac gaa caa tct ggt tat cgt<br>Ser Gly Tyr Arg Thr Asp Gly Val Leu Tyr Glu Gln Ser Gly Tyr Arg<br>1185               1190               1195               1200 | 3600 |
| aca gac gga gta cca tgc gaa caa cat ggt tgt cat aca gac gga gta<br>Thr Asp Gly Val Pro Cys Glu Gln His Gly Cys His Thr Asp Gly Val<br>             1205               1210               1215 | 3648 |
| cca tac aaa caa cat ggt tgt cat aca gac aga tca aga gat gaa caa<br>Pro Tyr Lys Gln His Gly Cys His Thr Asp Arg Ser Arg Asp Glu Gln<br>1220               1225               1230 | 3696 |
| ctt ggt tat gtg aca aaa acg att gat gta ttc cct gat aca gat aaa<br>Leu Gly Tyr Val Thr Lys Thr Ile Asp Val Phe Pro Asp Thr Asp Lys<br>             1235               1240               1245 | 3744 |
| gta cgt atc gac att gga gaa acc gaa ggt acc ttt aaa gta gaa agt<br>Val Arg Ile Asp Ile Gly Glu Thr Glu Gly Thr Phe Lys Val Glu Ser<br>1250               1255               1260 | 3792 |
| gtg gaa ctg att tgt atg gaa gag taa<br>Val Glu Leu Ile Cys Met Glu Glu<br>1265               1270 | 3819 |

<210> SEQ ID NO 2
<211> LENGTH: 1272
<212> TYPE: PRT
<213> ORGANISM: Brevibacillus

<400> SEQUENCE: 2

Met Asn Gln Asn Gln Asn Gln Asn Gln Asn Lys Asn Glu Leu
 1               5                  10                  15

Gln Ile Ile Glu Pro Ser Ser Asp Ser Phe Leu Tyr Ser His Asn Asn
             20                  25                  30

Tyr Pro Tyr Ser Thr Asp Pro Asn Thr Val Leu His Gly Arg Asn Tyr
         35                  40                  45

Lys Glu Trp Leu Asn Met Cys Thr Gly Thr Asp Asp Ser Arg Gly Pro
     50                  55                  60

Glu Ala Ala Ser Thr Ala Arg Ser Ala Ile Ser Val Ala Ile Thr Ile
 65                  70                  75                  80

Ser Thr Thr Ile Leu Gly Leu Gly Val Pro Phe Ala Ser Gln Ile
                 85                  90                  95

Gly Ala Phe Tyr Asn Phe Val Leu Asn Thr Val Trp Pro Gln Gly Asn
            100                 105                 110

Asn Gln Trp Glu Glu Phe Met Arg His Val Glu Asn Leu Ile Asn Glu
        115                 120                 125

Arg Ile Ala Asp Tyr Ala Arg Ser Lys Ala Leu Ala Glu Leu Thr Gly
    130                 135                 140

Leu Gly Asn Asn Leu Asn Leu Tyr Arg Glu Ala Phe Glu Asp Trp Arg
145                 150                 155                 160

Arg Asn Pro Thr Ser Gln Glu Ala Lys Thr Arg Val Ile Asp Arg Phe
                165                 170                 175

Arg Ile Leu Asp Gly Leu Phe Glu Ala Tyr Met Pro Ser Phe Ala Val
            180                 185                 190

```
Gln Gly Phe Glu Val Gln Leu Leu Thr Val Tyr Ala Ser Ala Ala Asn
        195                 200                 205

Ile His Leu Phe Leu Leu Arg Asp Ser Ser Ile Tyr Gly Leu Asp Trp
210                 215                 220

Gly Leu Ser Gln Thr Asn Val Asn Glu Asn Tyr Asn Arg Gln Ile Arg
225                 230                 235                 240

His Thr Ala Thr Tyr Ala Asn His Cys Thr Thr Trp Tyr Gln Thr Gly
                245                 250                 255

Leu Gln Arg Leu Gln Gly Thr Asn Ala Thr Ser Trp Gly Ala Tyr Asn
                260                 265                 270

Arg Phe Arg Arg Glu Met Thr Leu Thr Val Leu Asp Ile Ser Ser Leu
        275                 280                 285

Phe Ser Asn Tyr Asp Tyr Arg Ser Tyr Pro Thr Glu Val Arg Gly Glu
        290                 295                 300

Leu Thr Arg Glu Ile Tyr Thr Asp Pro Val Gly Phe Gly Trp Gln Asn
305                 310                 315                 320

Asn Ala Pro Ser Phe Ala Glu Ile Glu Asn Leu Ala Ile Arg Ala Pro
                325                 330                 335

Arg Thr Val Thr Trp Leu Asn Ser Thr Arg Ile His Thr Gly Thr Leu
                340                 345                 350

Gln Gly Trp Ser Gly Ser Asn Arg Tyr Trp Ala Ala His Met Gln Asn
        355                 360                 365

Phe Ser Glu Thr Asn Ser Gly Asn Ile Arg Phe Asp Gly Pro Leu Tyr
        370                 375                 380

Gly Ser Thr Val Gly Thr Ile Ile Arg Thr Asp Asn Tyr Glu Met Gly
385                 390                 395                 400

Asn Arg Asp Ile Tyr Thr Ile Thr Ser Glu Ala Val Gly Ala Leu Trp
                405                 410                 415

Pro His Gly Gln Thr Val Leu Gly Val Ala Ser Ala Arg Phe Thr Leu
                420                 425                 430

Arg His Leu Ser Asn Asn Phe Thr Gln Val Leu Val Tyr Glu Asn Pro
        435                 440                 445

Ile Ser Asn Ser Phe Asn Arg Ser Thr Val Thr Ser Glu Leu Pro Gly
        450                 455                 460

Glu Asn Ser Asp Arg Pro Thr Asp Ser Asp Tyr Ser His Arg Leu Thr
465                 470                 475                 480

Cys Ile Thr Ala Phe Arg Ala Gly Asn Asn Gly Thr Val Pro Val Phe
                485                 490                 495

Gly Trp Thr Ser Arg Thr Val Asn Arg Asp Asn Ile Ile Glu Gln Asn
                500                 505                 510

Lys Ile Thr Gln Phe Pro Gly Val Lys Ser His Thr Leu Asn Asn Cys
        515                 520                 525

Gln Val Val Arg Gly Thr Gly Phe Thr Gly Gly Asp Trp Leu Arg Pro
        530                 535                 540

Asn Asn Asn Gly Thr Phe Arg Leu Thr Ile Thr Ser Phe Ser Ser Gln
545                 550                 555                 560

Ser Tyr Arg Ile Arg Leu Arg Tyr Ala Thr Ser Val Gly Asn Thr Ser
                565                 570                 575

Leu Val Ile Ser Ser Asp Ala Gly Ile Ser Ser Thr Thr Ile Pro
                580                 585                 590

Leu Thr Ser Thr Ile Thr Ser Leu Pro Gln Thr Val Pro Tyr Gln Ala
        595                 600                 605
```

-continued

```
Phe Arg Val Val Asp Leu Pro Ile Thr Phe Thr Thr Pro Thr Thr Gln
610                 615                 620
Arg Asn Tyr Thr Phe Asp Phe Arg Leu Gln Asn Pro Ser Asn Ala Asn
625                 630                 635                 640
Val Phe Ile Asp Arg Phe Glu Phe Val Pro Ile Gly Gly Ser Leu Ser
            645                 650                 655
Glu Tyr Glu Thr Lys His Gln Leu Glu Lys Ala Arg Lys Ala Val Asn
                660                 665                 670
Asp Leu Phe Thr Asn Glu Ser Lys Asn Val Leu Lys Lys Glu Thr Thr
        675                 680                 685
Asp Tyr Asp Ile Asp Gln Ala Ala Asn Leu Val Glu Cys Ile Ser Asp
690                 695                 700
Glu Cys Ala Asn Ala Lys Met Ile Leu Leu Asp Glu Val Lys Tyr Ala
705                 710                 715                 720
Lys Gln Leu Ser Glu Ala Arg Asn Leu Leu Leu Asn Gly Asn Phe Glu
            725                 730                 735
Tyr Gln Asp Arg Asp Gly Glu Asn Pro Trp Lys Thr Ser Pro Asn Val
                740                 745                 750
Thr Ile Gln Glu Asn Asn Pro Ile Phe Lys Gly Arg Tyr Leu Ser Met
        755                 760                 765
Ser Gly Ala Asn Asn Ile Glu Val Thr Asn Asp Ile Phe Pro Thr Tyr
770                 775                 780
Ala Tyr Gln Lys Ile Asp Glu Ser Lys Leu Lys Pro Tyr Thr Arg Tyr
785                 790                 795                 800
Lys Val Arg Gly Phe Val Gly Asn Ser Lys Asp Leu Glu Leu Leu Ile
            805                 810                 815
Thr Arg Tyr Asn Glu Glu Val Asp Ala Ile Leu Asn Val Ala Asn Asp
                820                 825                 830
Ile Pro His Ala Pro Thr Pro Phe Cys Gly Gly Phe Asp Arg Cys Lys
        835                 840                 845
Pro His Ser Tyr Pro Pro Met Asn Pro Glu Cys His His Asp Val Ile
850                 855                 860
Asn Asn Ile Glu Ile Ser Ser Pro Cys His His Asn Lys Met Val Asp
865                 870                 875                 880
Asn Ala Asp Thr Ser Ser Arg His Ser Glu Leu Gly Lys Lys His Gly
            885                 890                 895
Ile Cys His Glu Ser His His Phe Glu Phe His Ile Asp Thr Gly Lys
                900                 905                 910
Ile Asp Leu Val Glu Asn Leu Gly Ile Trp Val Ile Phe Lys Ile Cys
        915                 920                 925
Ser Thr Asp Gly Tyr Ala Thr Leu Asp Asn Leu Glu Val Ile Glu Glu
930                 935                 940
Gly Pro Leu Gly Ala Glu Ser Leu Glu Arg Val Lys Arg Arg Glu Lys
945                 950                 955                 960
Lys Trp Lys His His Met Glu His Lys Cys Ser Glu Thr Lys His Val
            965                 970                 975
Tyr His Ala Ala Lys Gln Ala Val Val Ala Leu Phe Thr Asn Thr Gln
                980                 985                 990
Tyr Asp Arg Leu Lys Phe Glu Thr Thr Ile Ser Asn Ile Leu Phe Ala
        995                 1000                1005
Asp Tyr Leu Val Ser Ser Ile Pro Phe Val Tyr Asn Lys Trp Leu Pro
1010                1015                1020
Asp Val Pro Gly Met Asn Tyr Asp Ile Tyr Thr Glu Leu Lys Asn Leu
```

```
                1025              1030              1035              1040
        Ile Thr Gly Ala Phe Asn Leu Tyr Asp Gln Arg Asn Ile Ile Lys Asn
                        1045              1050              1055

Gly Asp Phe Asn Asn Gly Leu Met His Trp His Ala Thr Pro His Ala
                        1060              1065              1070

Arg Val Glu Gln Ile Asp Asn Arg Ser Val Leu Val Leu Pro Asn Tyr
                        1075              1080              1085

Ala Ala Asn Val Ser Gln Glu Val Cys Leu Glu His Asn Arg Gly Tyr
                        1090              1095              1100

Val Leu Arg Val Thr Ala Lys Lys Glu Gly Pro Gly Ile Gly Tyr Val
        1105              1110              1115              1120

Thr Phe Ser Asp Cys Ala Asn Asn Ile Glu Lys Leu Thr Phe Thr Ser
                        1125              1130              1135

Cys Asp Tyr Gly Thr Asn Glu Val Pro Tyr Glu Gln Ser Asn Tyr Pro
                        1140              1145              1150

Thr Asp Gly Val Ser Tyr Gly Gln His Gly Cys Asn Ile Asp Arg Val
                        1155              1160              1165

Pro Tyr Glu Gln Ser Gly Tyr Pro Thr Asp Gly Val Ser Tyr Glu Gln
                        1170              1175              1180

Ser Gly Tyr Arg Thr Asp Gly Val Leu Tyr Glu Gln Ser Gly Tyr Arg
        1185              1190              1195              1200

Thr Asp Gly Val Pro Cys Glu Gln His Gly Cys His Thr Asp Gly Val
                        1205              1210              1215

Pro Tyr Lys Gln His Gly Cys His Thr Asp Arg Ser Arg Asp Glu Gln
                        1220              1225              1230

Leu Gly Tyr Val Thr Lys Thr Ile Asp Val Phe Pro Asp Thr Asp Lys
                        1235              1240              1245

Val Arg Ile Asp Ile Gly Glu Thr Glu Gly Thr Phe Lys Val Glu Ser
                        1250              1255              1260

Val Glu Leu Ile Cys Met Glu Glu
        1265              1270

<210> SEQ ID NO 3
<211> LENGTH: 1953
<212> TYPE: DNA
<213> ORGANISM: Brevibacillus
<220> FEATURE:
<221> NAME/KEY: CDS
<222> LOCATION: (1)...(1953)

<400> SEQUENCE: 3 atg aat caa aat caa aat cag aat cag aat caa aat aaa aat gaa ctt      48
Met Asn Gln Asn Gln Asn Gln Asn Gln Asn Gln Asn Lys Asn Glu Leu
1               5                   10                  15 caa atc ata gaa cct tca agc gat tct ttt ctt tat agt cac aac aat      96
Gln Ile Ile Glu Pro Ser Ser Asp Ser Phe Leu Tyr Ser His Asn Asn
            20                  25                  30 tat ccg tat tcc act gat cca aat aca gta tta cac ggt agg aat tac     144
Tyr Pro Tyr Ser Thr Asp Pro Asn Thr Val Leu His Gly Arg Asn Tyr
        35                  40                  45 aaa gag tgg cta aac atg tgt aca ggt aca gac gat tca cga ggt ccc     192
Lys Glu Trp Leu Asn Met Cys Thr Gly Thr Asp Asp Ser Arg Gly Pro
    50                  55                  60 gaa gct gct tct act gca aga tca gct ata tcg gtt gcg att act ata     240
Glu Ala Ala Ser Thr Ala Arg Ser Ala Ile Ser Val Ala Ile Thr Ile
65                  70                  75                  80 agc acc aca att ctt ggc tta cta ggt gtt ccg ttt gca tct cag atc     288
```

```
Ser Thr Thr Ile Leu Gly Leu Leu Gly Val Pro Phe Ala Ser Gln Ile
                85              90              95 ggg gca ttt tat aac ttc gta ttg aat acg gta tgg cct cag gga aat    336
Gly Ala Phe Tyr Asn Phe Val Leu Asn Thr Val Trp Pro Gln Gly Asn
            100             105             110 aac caa tgg gaa gag ttc atg aga cat gta gaa aat ctc ata aac gaa    384
Asn Gln Trp Glu Glu Phe Met Arg His Val Glu Asn Leu Ile Asn Glu
            115             120             125 cga ata gct gat tat gca aga agt aag gca ctt gca gaa tta acg ggt    432
Arg Ile Ala Asp Tyr Ala Arg Ser Lys Ala Leu Ala Glu Leu Thr Gly
130             135             140 tta ggt aat aac tta aat tta tat aga gag gct ttt gaa gat tgg aga    480
Leu Gly Asn Asn Leu Asn Leu Tyr Arg Glu Ala Phe Glu Asp Trp Arg
145             150             155             160 cga aat cct act agt caa gaa gct aaa acc cgc gta ata gat aga ttc    528
Arg Asn Pro Thr Ser Gln Glu Ala Lys Thr Arg Val Ile Asp Arg Phe
                165             170             175 cgt ata cta gat ggc tta ttt gaa gca tat atg cca tca ttt gca gta    576
Arg Ile Leu Asp Gly Leu Phe Glu Ala Tyr Met Pro Ser Phe Ala Val
            180             185             190 caa ggt ttt gaa gta caa tta tta aca gtg tat gca tcc gct gca aat    624
Gln Gly Phe Glu Val Gln Leu Leu Thr Val Tyr Ala Ser Ala Ala Asn
            195             200             205 atc cat tta ttt tta tta aga gat agc tct att tac ggt ttg gat tgg    672
Ile His Leu Phe Leu Leu Arg Asp Ser Ser Ile Tyr Gly Leu Asp Trp
210             215             220 gga tta agt caa act aat gtt aac gaa aat tac aat cgc caa ata agg    720
Gly Leu Ser Gln Thr Asn Val Asn Glu Asn Tyr Asn Arg Gln Ile Arg
225             230             235             240 cac acc gca acg tat gca aat cat tgt aca act tgg tat caa act ggt    768
His Thr Ala Thr Tyr Ala Asn His Cys Thr Thr Trp Tyr Gln Thr Gly
                245             250             255 tta caa aga ttg caa ggt acc aat gct acc agt tgg ggc gct tat aat    816
Leu Gln Arg Leu Gln Gly Thr Asn Ala Thr Ser Trp Gly Ala Tyr Asn
            260             265             270 aga ttt aga agg gaa atg acg tta aca gta tta gat att agt tca tta    864
Arg Phe Arg Arg Glu Met Thr Leu Thr Val Leu Asp Ile Ser Ser Leu
            275             280             285 ttt tca aat tat gat tat cgt agt tat cca aca gag gta agg gga gag    912
Phe Ser Asn Tyr Asp Tyr Arg Ser Tyr Pro Thr Glu Val Arg Gly Glu
290             295             300 ctt acg aga gaa att tat acg gat cca gta ggc ttt ggc tgg cag aat    960
Leu Thr Arg Glu Ile Tyr Thr Asp Pro Val Gly Phe Gly Trp Gln Asn
305             310             315             320 aat gca cca tca ttc gct gaa ata gaa aat cta gca att agg gca cca   1008
Asn Ala Pro Ser Phe Ala Glu Ile Glu Asn Leu Ala Ile Arg Ala Pro
                325             330             335 aga acc gtt act tgg tta aat tca aca aga att cat aca ggg acc ttg   1056
Arg Thr Val Thr Trp Leu Asn Ser Thr Arg Ile His Thr Gly Thr Leu
            340             345             350 cag ggc tgg agt ggt tct aac aga tat tgg gca gct cac atg caa aac   1104
Gln Gly Trp Ser Gly Ser Asn Arg Tyr Trp Ala Ala His Met Gln Asn
            355             360             365 ttt tca gaa acc aat tca gga aat ata aga ttt gac ggt cct ctc tat   1152
Phe Ser Glu Thr Asn Ser Gly Asn Ile Arg Phe Asp Gly Pro Leu Tyr
            370             375             380 ggg tcg acg gta ggt act att att cgt act gat aat tac gaa atg ggg   1200
Gly Ser Thr Val Gly Thr Ile Ile Arg Thr Asp Asn Tyr Glu Met Gly
385             390             395             400
```

```
aac cga gat att tac acc att act tca gaa gct gtt ggc gcc ctt tgg       1248
Asn Arg Asp Ile Tyr Thr Ile Thr Ser Glu Ala Val Gly Ala Leu Trp
            405                 410                 415 cca cat ggt caa act gtg ttg gga gtc gct tcg gct aga ttt act tta       1296
Pro His Gly Gln Thr Val Leu Gly Val Ala Ser Ala Arg Phe Thr Leu
        420                 425                 430 aga cat ctt tcc aat aat ttt aca cag gtg ctg gtg tat gag aat cca       1344
Arg His Leu Ser Asn Asn Phe Thr Gln Val Leu Val Tyr Glu Asn Pro
    435                 440                 445 ata agt aat agt ttt aat aga tca act gta act agt gaa tta cct gga       1392
Ile Ser Asn Ser Phe Asn Arg Ser Thr Val Thr Ser Glu Leu Pro Gly
450                 455                 460 gaa aac tca gat agg cca act gat agc gat tat agt cat aga cta acg       1440
Glu Asn Ser Asp Arg Pro Thr Asp Ser Asp Tyr Ser His Arg Leu Thr
465                 470                 475                 480 tgt atc aca gct ttt cga gct gga aat aat ggt acg gtt cca gta ttt       1488
Cys Ile Thr Ala Phe Arg Ala Gly Asn Asn Gly Thr Val Pro Val Phe
            485                 490                 495 ggc tgg aca tct aga act gtt aat cgc gac aat ata att gag caa aac       1536
Gly Trp Thr Ser Arg Thr Val Asn Arg Asp Asn Ile Ile Glu Gln Asn
        500                 505                 510 aaa att aca caa ttc cca ggt gtt aag tca cac act ctc aac aat tgt       1584
Lys Ile Thr Gln Phe Pro Gly Val Lys Ser His Thr Leu Asn Asn Cys
    515                 520                 525 caa gta gtt aga ggg act gga ttt act gga gga gac tgg ttg aga cca       1632
Gln Val Val Arg Gly Thr Gly Phe Thr Gly Gly Asp Trp Leu Arg Pro
530                 535                 540 aat aat aat ggt aca ttt aga cta act att act tca ttc tcg agc caa       1680
Asn Asn Asn Gly Thr Phe Arg Leu Thr Ile Thr Ser Phe Ser Ser Gln
545                 550                 555                 560 tct tac cga atc cgc tta cgt tat gct act tca gta ggg aat act tct       1728
Ser Tyr Arg Ile Arg Leu Arg Tyr Ala Thr Ser Val Gly Asn Thr Ser
            565                 570                 575 tta gtt ata tct tct tct gat gca ggt att tct tcc aca aca att ccg       1776
Leu Val Ile Ser Ser Ser Asp Ala Gly Ile Ser Ser Thr Thr Ile Pro
        580                 585                 590 ctt act tca aca ata aca tca ctg ccc caa act gta cca tac cag gct       1824
Leu Thr Ser Thr Ile Thr Ser Leu Pro Gln Thr Val Pro Tyr Gln Ala
    595                 600                 605 ttt agg gtt gta gat tta cct att act ttt aca aca cct act acc caa       1872
Phe Arg Val Val Asp Leu Pro Ile Thr Phe Thr Thr Pro Thr Thr Gln
610                 615                 620 aga aat tat acg ttt gat ttc cgt ctc caa aat cca tct aac gca aat       1920
Arg Asn Tyr Thr Phe Asp Phe Arg Leu Gln Asn Pro Ser Asn Ala Asn
625                 630                 635                 640 gta ttc att gat aga ttt gaa ttt gtt cca att                           1953
Val Phe Ile Asp Arg Phe Glu Phe Val Pro Ile
            645                 650

<210> SEQ ID NO 4
<211> LENGTH: 651
<212> TYPE: PRT
<213> ORGANISM: Brevibacillus

<400> SEQUENCE: 4

Met Asn Gln Asn Gln Asn Gln Asn Gln Asn Lys Asn Glu Leu
  1               5                  10                  15

Gln Ile Ile Glu Pro Ser Ser Asp Ser Phe Leu Tyr Ser His Asn Asn
             20                  25                  30

Tyr Pro Tyr Ser Thr Asp Pro Asn Thr Val Leu His Gly Arg Asn Tyr
```

```
            35                  40                  45
Lys Glu Trp Leu Asn Met Cys Thr Gly Thr Asp Asp Ser Arg Gly Pro
 50                  55                  60
Glu Ala Ala Ser Thr Ala Arg Ser Ala Ile Ser Val Ala Ile Thr Ile
 65                  70                  75                  80
Ser Thr Thr Ile Leu Gly Leu Gly Val Pro Phe Ala Ser Gln Ile
                     85                  90                  95
Gly Ala Phe Tyr Asn Phe Val Leu Asn Thr Val Trp Pro Gln Gly Asn
                100                 105                 110
Asn Gln Trp Glu Glu Phe Met Arg His Val Glu Asn Leu Ile Asn Glu
            115                 120                 125
Arg Ile Ala Asp Tyr Ala Arg Ser Lys Ala Leu Ala Glu Leu Thr Gly
        130                 135                 140
Leu Gly Asn Asn Leu Asn Leu Tyr Arg Glu Ala Phe Glu Asp Trp Arg
145                 150                 155                 160
Arg Asn Pro Thr Ser Gln Glu Ala Lys Thr Arg Val Ile Asp Arg Phe
                    165                 170                 175
Arg Ile Leu Asp Gly Leu Phe Glu Ala Tyr Met Pro Ser Phe Ala Val
                180                 185                 190
Gln Gly Phe Glu Val Gln Leu Leu Thr Val Tyr Ala Ser Ala Ala Asn
            195                 200                 205
Ile His Leu Phe Leu Leu Arg Asp Ser Ser Ile Tyr Gly Leu Asp Trp
        210                 215                 220
Gly Leu Ser Gln Thr Asn Val Asn Glu Asn Tyr Asn Arg Gln Ile Arg
225                 230                 235                 240
His Thr Ala Thr Tyr Ala Asn His Cys Thr Thr Trp Tyr Gln Thr Gly
                    245                 250                 255
Leu Gln Arg Leu Gln Gly Thr Asn Ala Thr Ser Trp Gly Ala Tyr Asn
                260                 265                 270
Arg Phe Arg Arg Glu Met Thr Leu Thr Val Leu Asp Ile Ser Ser Leu
            275                 280                 285
Phe Ser Asn Tyr Asp Tyr Arg Ser Tyr Pro Thr Glu Val Arg Gly Glu
        290                 295                 300
Leu Thr Arg Glu Ile Tyr Thr Asp Pro Val Gly Phe Gly Trp Gln Asn
305                 310                 315                 320
Asn Ala Pro Ser Phe Ala Glu Ile Glu Asn Leu Ala Ile Arg Ala Pro
                    325                 330                 335
Arg Thr Val Thr Trp Leu Asn Ser Thr Arg Ile His Thr Gly Thr Leu
                340                 345                 350
Gln Gly Trp Ser Gly Ser Asn Arg Tyr Trp Ala Ala His Met Gln Asn
            355                 360                 365
Phe Ser Glu Thr Asn Ser Gly Asn Ile Arg Phe Asp Gly Pro Leu Tyr
        370                 375                 380
Gly Ser Thr Val Gly Thr Ile Ile Arg Thr Asp Asn Tyr Glu Met Gly
385                 390                 395                 400
Asn Arg Asp Ile Tyr Thr Ile Thr Ser Glu Ala Val Gly Ala Leu Trp
                    405                 410                 415
Pro His Gly Gln Thr Val Leu Gly Val Ala Ser Ala Arg Phe Thr Leu
                420                 425                 430
Arg His Leu Ser Asn Asn Phe Thr Gln Val Leu Val Tyr Glu Asn Pro
            435                 440                 445
Ile Ser Asn Ser Phe Asn Arg Ser Thr Val Thr Ser Glu Leu Pro Gly
        450                 455                 460
```

```
Glu Asn Ser Asp Arg Pro Thr Asp Ser Asp Tyr Ser His Arg Leu Thr
465                 470                 475                 480

Cys Ile Thr Ala Phe Arg Ala Gly Asn Asn Gly Thr Val Pro Val Phe
            485                 490                 495

Gly Trp Thr Ser Arg Thr Val Asn Arg Asp Asn Ile Ile Glu Gln Asn
                500                 505                 510

Lys Ile Thr Gln Phe Pro Gly Val Lys Ser His Thr Leu Asn Asn Cys
        515                 520                 525

Gln Val Val Arg Gly Thr Gly Phe Thr Gly Gly Asp Trp Leu Arg Pro
530                 535                 540

Asn Asn Asn Gly Thr Phe Arg Leu Thr Ile Thr Ser Phe Ser Ser Gln
545                 550                 555                 560

Ser Tyr Arg Ile Arg Leu Arg Tyr Ala Thr Ser Val Gly Asn Thr Ser
                565                 570                 575

Leu Val Ile Ser Ser Ser Asp Ala Gly Ile Ser Ser Thr Thr Ile Pro
            580                 585                 590

Leu Thr Ser Thr Ile Thr Ser Leu Pro Gln Thr Val Pro Tyr Gln Ala
        595                 600                 605

Phe Arg Val Val Asp Leu Pro Ile Thr Phe Thr Pro Thr Thr Gln
610                 615                 620

Arg Asn Tyr Thr Phe Asp Phe Arg Leu Gln Asn Pro Ser Asn Ala Asn
625                 630                 635                 640

Val Phe Ile Asp Arg Phe Glu Phe Val Pro Ile
                645                 650

<210> SEQ ID NO 5
<211> LENGTH: 4150
<212> TYPE: DNA
<213> ORGANISM: Brevibacillus

<400> SEQUENCE: 5
ttttactgac ccacattcca agaaatctc actttgttgt gatgggagcg tatgtgtaga      60
tcatgtactc aagtgtagtg tcggatgttt accagacgtt catttagatt gtcaatatgt     120
aactgtatgt gatctacaaa tgaccctgt tcatgagaga gcttgtcaat tgttaagat      180 tactggagaa tttcaatttt cctccattta ataagtacg aattttgttg ttaaacaccc     240
attattaata aatgggtaac aaataggagg gtaaatga atcaaaatca aaatcagaat      300
cagaatcaaa ataaaaatga acttcaaatc atagaacctt caagcgattc ttttctttat    360
agtcacaaca attatccgta ttccactgat ccaaatacag tattcacgg taggaattac      420 aaagagtggc taaacatgtg tacaggtaca gacgattcac gaggtcccga agctgcttct    480
actgcaagat cagctatatc ggttgcgatt actataagca ccacaattct tggcttacta    540
ggtgttccgt ttgcatctca gatcggggca ttttataact tcgtattgaa tacggtatgg    600
cctcagggaa ataaccaatg gaagagttc atgagacatg tagaaaatct cataaacgaa     660
cgaatagctg attatgcaag aagtaaggca cttgcagaat taacgggttt aggtaataac    720
ttaaatttat atagagaggc ttttgaagat tggagacgaa atcctactag tcaagaagct    780
aaaacccgcg taatagatag attccgtata ctagatggct tatttgaagc atatatgcca    840
tcatttgcag tacaaggttt tgaagtacaa ttattaacag tgtatgcatc cgctgcaaat    900
atccatttat ttttattaag agatagctct atttacggtt tggattgggg attaagtcaa    960
actaatgtta acgaaaatta caatcgccaa ataaggcaca ccgcaacgta tgcaaatcat   1020
```

```
tgtacaactt ggtatcaaac tggtttacaa agattgcaag gtaccaatgc taccagttgg    1080
ggcgcttata atagatttag aagggaaatg acgttaacag tattagatat tagttcatta    1140
ttttcaaatt atgattatcg tagttatcca acagaggtaa ggggagagct tacgagagaa    1200
atttatacgg atccagtagg ctttggctgg cagaataatg caccatcatt cgctgaaata    1260
gaaaatctag caattagggc accaagaacc gttacttggt taaattcaac aagaattcat    1320
acagggacct gcagggctg gagtggttct aacagatatt gggcagctca catgcaaaac    1380
ttttcagaaa ccaattcagg aaatataaga tttgacggtc ctctctatgg gtcgacggta    1440
ggtactatta ttcgtactga taattacgaa atggggaacc gagatatta caccattact    1500 tcagaagctg ttggcgccct ttggccacat ggtcaaactg tgttgggagt cgcttcggct    1560
agatttactt taagacatct ttccaataat tttacacagg tgctggtgta tgagaatcca    1620
ataagtaata gttttaatag atcaactgta actagtgaat tacctggaga aaactcagat    1680
aggccaactg atagcgatta tagtcataga ctaacgtgta tcacagcttt tcgagctgga    1740
aataatggta cggttccagt atttggctgg acatctagaa ctgttaatcg cgacaatata    1800
attgagcaaa acaaaattac acaattccca ggtgttaagt cacacactct caacaattgt    1860
caagtagtta gagggactgg atttactgga ggagactggt tgagaccaaa taataatggt    1920
acatttagac taactattac ttcattctcg agccaatctt accgaatccg cttacgttat    1980
gctacttcag tagggaatac ttctttagtt atatcttctt ctgatgcagg tatttcttcc    2040
acaacaattc cgcttacttc aacaataaca tcactgcccc aaactgtacc ataccaggct    2100
tttagggttg tagatttacc tattactttt acaacaccta ctacccaaag aaattatacg    2160
tttgatttcc gtctccaaaa tccatctaac gcaaatgtat tcattgatag atttgaattt    2220
gttccaattg ggggttcttt gtctgagtat gaaaccaaac atcagctaga aaaagcaagg    2280
aaagcggtga acgatttgtt taccaatgaa tcgaaaaatg tgttaaaaaa agaaactact    2340
gattatgaca tagatcaagc agcaaacttg gtagaatgta tcagatga atgtgcaaat    2400 gcaaaaatga tcctattaga tgaagtaaaa tatgcgaaac aactcagcga agcccgcaat    2460
ctacttctaa atggtaattt tgaataccaa gatagagatg gggagaatcc atggaaaaca    2520
agtcccaatg ttaccatcca agagaataat cccatttta aaggccgtta tctcagtatg    2580
tcgggtgcga acaatatcga ggtaacaaat gatatattcc ccacttatgc ataccaaaaa    2640
attgatgaat ccaaattaaa accctatacg cgttataaag ttcgagggtt tgttggaaat    2700
agtaaagatt tagagttgtt gattacacga tataatgaag aagtagatgc gattttaaat    2760
gtagcaaatg atataccaca tgctccgaca cctttctgcg gtggatttga tcgatgcaag    2820
ccacattctt atcctcctat gaatccagaa tgtcaccatg atgtaataaa taacattgaa    2880
atatcctctc cttgccatca caataagatg gttgataacg ctgatacatc ttctcgccat    2940
agtgaattag gtaaaaaaca tggcatttgt catgaatctc atcatttga attccatatt    3000 gatacaggaa aaatcgattt ggtcgaaaat ttgggaattt gggttatatt taaaatatgt    3060
tccacagatg gttacgcaac attagataat ttggaagtta ttgaagaggg tcctttagga    3120
gccgaatcat tagaacgtgt gaaaagaaga gaaaagaaat ggaaacatca catgaacac    3180 aagtgttcag aaactaaaca tgtataccat gctgcgaaac aagcggtggt ggcgttattc    3240
acaaacactc aatatgatag attgaagttc gaaacaacca tatccaatat tctatttgct    3300
gattatctcg tgtcgtcaat tccgtttgta tataataaat ggttaccaga tgttccaggt    3360
atgaattatg atatctatac agaattaaaa aatctgatta cgggagcttt caatctatac    3420
```

-continued

```
gatcaacgaa atattataaa aaatggagac tttaataacg gactcatgca ttggcatgcg    3480
acacctcatg cgagagtaga gcaaatagat aataggtctg tgctggtgct tccaaattat    3540
gctgccaatg tttcacaaga ggtttgttta gaacacaatc gtggttatgt attacgtgta    3600
acggcgaaaa aagaaggtcc tggaattgga tatgttacgt tcagtgattg tgcaaataat    3660
atagaaaaac tgacatttac ttcttgcgat tatggtacaa cgaagtgcc atatgagcaa     3720 tctaattatc ctacagacgg agtttcatac ggacaacatg ttgtaatat agacagagta     3780 ccgtacgaac aatctggtta tcctacagac ggagtatcgt acgaacaatc tggttatcgt    3840
acagacggag tactgtacga acaatctggt tatcgtacag acggagtacc atgcgaacaa    3900
catggttgtc atacagacgg agtaccatac aaacaacatg ttgtcatac agacagatca     3960 agagatgaac aacttggtta tgtgacaaaa acgattgatg tattccctga tacagataaa    4020
gtacgtatcg acattggaga aaccgaaggt acctttaaag tagaaagtgt ggaactgatt    4080
tgtatggaag agtaaatcat aacaaagtaa aaggtatggt ttaatcaaaa atttattttc    4140
cgaacaacag                                                           4150

<210> SEQ ID NO 6
<211> LENGTH: 1059
<212> TYPE: DNA
<213> ORGANISM: Brevibacillus
<220> FEATURE:
<221> NAME/KEY: CDS
<222> LOCATION: (1)...(1059)

<400> SEQUENCE: 6 atg atg gaa cca atg aag ttt cgg aaa aat ggt tta tat aat att gta          48
Met Met Glu Pro Met Lys Phe Arg Lys Asn Gly Leu Tyr Asn Ile Val
1               5                   10                  15 aat gta aac agt gga aat cta gca gtt gta aaa gat gca tca aaa gaa          96
Asn Val Asn Ser Gly Asn Leu Ala Val Val Lys Asp Ala Ser Lys Glu
            20                  25                  30 aat tat gca cct att att caa ttt gat aaa cgg ggc aca gat aat gaa         144
Asn Tyr Ala Pro Ile Ile Gln Phe Asp Lys Arg Gly Thr Asp Asn Glu
        35                  40                  45 aaa ttt gtg ttc ttt cct ttg gat agt aaa ggt aaa agt caa aca tat         192
Lys Phe Val Phe Phe Pro Leu Asp Ser Lys Gly Lys Ser Gln Thr Tyr
    50                  55                  60 gca att gcc gct tac cat agt gga aag att ata tgt gta aaa gat gca         240
Ala Ile Ala Ala Tyr His Ser Gly Lys Ile Ile Cys Val Lys Asp Ala
65                  70                  75                  80 tca aca gaa aat tat gca cct att atc caa ttt aat tgg aat aac act         288
Ser Thr Glu Asn Tyr Ala Pro Ile Ile Gln Phe Asn Trp Asn Asn Thr
                85                  90                  95 aca aat gaa caa tgg aat att ata cct gat aat tcg tgg ggg tat aat         336
Thr Asn Glu Gln Trp Asn Ile Ile Pro Asp Asn Ser Trp Gly Tyr Asn
            100                 105                 110 atc gtg aat caa aac agt gga aat cta gca gtt gta aaa gat gca tca         384
Ile Val Asn Gln Asn Ser Gly Asn Leu Ala Val Val Lys Asp Ala Ser
        115                 120                 125 aaa gaa aat tat gca cct att att caa ttt gat aaa cgg ggc aca atg         432
Lys Glu Asn Tyr Ala Pro Ile Ile Gln Phe Asp Lys Arg Gly Thr Met
    130                 135                 140 aac gaa gat tgg aaa ttt caa gag gta agc tgg ttt cca gta cct gaa         480
Asn Glu Asp Trp Lys Phe Gln Glu Val Ser Trp Phe Pro Val Pro Glu
145                 150                 155                 160 act cct aca gta gaa act cta cca aaa gcc cct caa ttt aat gat gtt         528
Thr Pro Thr Val Glu Thr Leu Pro Lys Ala Pro Gln Phe Asn Asp Val
```

```
                Thr Pro Thr Val Glu Thr Leu Pro Lys Ala Pro Gln Phe Asn Asp Val
                                165                 170                 175 cat caa aat tta cct cag gta act gac gag ata ctt aca ggt tac gca         576
His Gln Asn Leu Pro Gln Val Thr Asp Glu Ile Leu Thr Gly Tyr Ala
            180                 185                 190 atg att cct tgc att atg gtt aga gac cat aat tgg tcc gat gaa tct         624
Met Ile Pro Cys Ile Met Val Arg Asp His Asn Trp Ser Asp Glu Ser
        195                 200                 205 aaa atg aaa act tct cct tac tat att ttg aaa aaa tat caa ttt tgg         672
Lys Met Lys Thr Ser Pro Tyr Tyr Ile Leu Lys Lys Tyr Gln Phe Trp
    210                 215                 220 gag ttg ttg gcg agt ttt cag ctt ttt aat ggt gaa act caa aag agg         720
Glu Leu Leu Ala Ser Phe Gln Leu Phe Asn Gly Glu Thr Gln Lys Arg
225                 230                 235                 240 act tat aag gtt ggt atg aat atg aca gat caa agg tca atg gaa aat         768
Thr Tyr Lys Val Gly Met Asn Met Thr Asp Gln Arg Ser Met Glu Asn
                245                 250                 255 tca att ggc aca atg att ggt gca gat gct ggt ttt caa ttt gat ggt         816
Ser Ile Gly Thr Met Ile Gly Ala Asp Ala Gly Phe Gln Phe Asp Gly
            260                 265                 270 cta act gat gcg ata aag tct gaa ata aca aca tca tta aaa gtt gca         864
Leu Thr Asp Ala Ile Lys Ser Glu Ile Thr Thr Ser Leu Lys Val Ala
        275                 280                 285 atc tct aga gaa aca aaa cta atg act gaa gaa acc ggg gag gta atc         912
Ile Ser Arg Glu Thr Lys Leu Met Thr Glu Glu Thr Gly Glu Val Ile
    290                 295                 300 aga gaa aat aaa act ggt aaa tta caa gca tat gca gag tat gta tgt         960
Arg Glu Asn Lys Thr Gly Lys Leu Gln Ala Tyr Ala Glu Tyr Val Cys
305                 310                 315                 320 gtt agt aaa ttt gtg cta gaa cgt aca gat gga aca gaa gta gct tct        1008
Val Ser Lys Phe Val Leu Glu Arg Thr Asp Gly Thr Glu Val Ala Ser
                325                 330                 335 tgg acc atg tcg aat cct aat aca ata agc aaa act gtg ttc cca gga        1056
Trp Thr Met Ser Asn Pro Asn Thr Ile Ser Lys Thr Val Phe Pro Gly
            340                 345                 350 taa                                                                    1059

<210> SEQ ID NO 7
<211> LENGTH: 352
<212> TYPE: PRT
<213> ORGANISM: Brevibacillus

<400> SEQUENCE: 7

Met Met Glu Pro Met Lys Phe Arg Lys Asn Gly Leu Tyr Asn Ile Val
1               5                   10                  15

Asn Val Asn Ser Gly Asn Leu Ala Val Val Lys Asp Ala Ser Lys Glu
            20                  25                  30

Asn Tyr Ala Pro Ile Ile Gln Phe Asp Lys Arg Gly Thr Asp Asn Glu
        35                  40                  45

Lys Phe Val Phe Pro Leu Asp Ser Lys Gly Lys Ser Gln Thr Tyr
    50                  55                  60

Ala Ile Ala Ala Tyr His Ser Gly Lys Ile Ile Cys Val Lys Asp Ala
65                  70                  75                  80

Ser Thr Glu Asn Tyr Ala Pro Ile Ile Gln Phe Asn Trp Asn Asn Thr
                85                  90                  95

Thr Asn Glu Gln Trp Asn Ile Ile Pro Asp Asn Ser Trp Gly Tyr Asn
            100                 105                 110

Ile Val Asn Gln Asn Ser Gly Asn Leu Ala Val Val Lys Asp Ala Ser
```

```
            115                 120                 125
Lys Glu Asn Tyr Ala Pro Ile Ile Gln Phe Asp Lys Arg Gly Thr Met
    130                 135                 140

Asn Glu Asp Trp Lys Phe Gln Glu Val Ser Trp Phe Pro Val Pro Glu
145                 150                 155                 160

Thr Pro Thr Val Glu Thr Leu Pro Lys Ala Pro Gln Phe Asn Asp Val
                165                 170                 175

His Gln Asn Leu Pro Gln Val Thr Asp Glu Ile Leu Thr Gly Tyr Ala
            180                 185                 190

Met Ile Pro Cys Ile Met Val Arg Asp His Asn Trp Ser Asp Glu Ser
        195                 200                 205

Lys Met Lys Thr Ser Pro Tyr Tyr Ile Leu Lys Lys Tyr Gln Phe Trp
    210                 215                 220

Glu Leu Leu Ala Ser Phe Gln Leu Phe Asn Gly Glu Thr Gln Lys Arg
225                 230                 235                 240

Thr Tyr Lys Val Gly Met Asn Met Thr Asp Gln Arg Ser Met Glu Asn
                245                 250                 255

Ser Ile Gly Thr Met Ile Gly Ala Asp Ala Gly Phe Gln Phe Asp Gly
            260                 265                 270

Leu Thr Asp Ala Ile Lys Ser Glu Ile Thr Thr Ser Leu Lys Val Ala
        275                 280                 285

Ile Ser Arg Glu Thr Lys Leu Met Thr Glu Glu Thr Gly Glu Val Ile
    290                 295                 300

Arg Glu Asn Lys Thr Gly Lys Leu Gln Ala Tyr Ala Glu Tyr Val Cys
305                 310                 315                 320

Val Ser Lys Phe Val Leu Glu Arg Thr Asp Gly Thr Glu Val Ala Ser
                325                 330                 335

Trp Thr Met Ser Asn Pro Asn Thr Ile Ser Lys Thr Val Phe Pro Gly
            340                 345                 350

<210> SEQ ID NO 8
<211> LENGTH: 1688
<212> TYPE: DNA
<213> ORGANISM: Brevibacillus

<400> SEQUENCE: 8
gcgagaatgc tgccacacta attcataaca tggctaaaaa attgggggta taagggatat      60
gaaaacaaca ggaaacaaag cggtattatt tgctggggtg cttggatcat taaagctatt     120
aactgaagcc tacggatata atattatttc tgacgaccag atcaacgcaa ttgtgaatgg     180
tctttcggct gtagtggctg taatagctgc ctttactaat aactttaaat caaaaaccga     240
ttagatcaaa ataccgttca gtcgagtgga ctctttcttt ttaaatatat acatatttgt     300
gaaaatatgt aataatacgt aatgatatgc aactaagtga ttttccttca gaatcatgtt     360
tctcattatt ttaccaccca aaaaattaa ggggagatta tgatggaacc aatgaagttt      420
cggaaaaatg gtttatataa tattgtaaat gtaaacagtg gaaatctagc agttgtaaaa     480
gatgcatcaa agaaaattta tgcacctatt attcaatttg ataaacgggg cacagataat     540
gaaaaatttg tgttctttcc tttggatagt aaagtaaaaa gtcaaacata tgcaattgcc     600
gcttaccata gtggaaagat tatatgtgta aaagatgcat caacagaaaa ttatgcacct     660
attatccaat taattggaa taacactaca aatgaacaat ggaatattat acctgataat     720
tcgtgggggt ataatatcgt gaatcaaaac agtggaaatc tagcagttgt aaaagatgca     780
tcaaaagaaa attatgcacc tattattcaa tttgataaac ggggcacaat gaacgaagat     840
```

-continued

```
tggaaatttc aagaggtaag ctggtttcca gtacctgaaa ctcctacagt agaaactcta    900
ccaaaagccc ctcaatttaa tgatgttcat caaaatttac ctcaggtaac tgacgagata    960
cttacaggtt acgcaatgat tccttgcatt atggttagag accataattg gtccgatgaa   1020
tctaaaatga aaacttctcc ttactatatt ttgaaaaaat atcaattttg ggagttgttg   1080
gcgagttttc agcttttaa tggtgaaact caaagagga cttataaggt tggtatgaat    1140
atgcagatc aaaggtcaat ggaaaattca attggcacaa tgattggtgc agatgctggt   1200
tttcaatttg atggtctaac tgatgcgata agtctgaaa taacaacatc attaaaagtt    1260
gcaatctcta gagaaacaaa actaatgact gaagaaaccg gggaggtaat cagagaaaat   1320
aaaactggta aattacaagc atatgcagag tatgtatgtg ttagtaaatt tgtgctagaa   1380
cgtacagatg aacagaagt agcttcttgg accatgtcga atcctaatac aataagcaaa    1440
actgtgttcc aggataaga aggagaaagc tctctgacgg aaattaaacc gttggagggc    1500
atttttatt gataaacatg taattttacc cattgcataa tctcctcata ttcaaataaa    1560
ataagaacac acattcgtat ttagagagat gttttgatgg ctagtaaaat tcttgatcca    1620
cttgtaacga aattcatctt gccagaacat gcagaaatgt tacgtcagta tcacgaggat    1680
aagaaact                                                           1688

<210> SEQ ID NO 9
<211> LENGTH: 1893
<212> TYPE: DNA
<213> ORGANISM: Brevibacillus
<220> FEATURE:
<221> NAME/KEY: CDS
<222> LOCATION: (1)...(1893)

<400> SEQUENCE: 9 atg cta cac aga aat aaa atg ctg aaa gtc ctg agt aca act acg atg     48
Met Leu His Arg Asn Lys Met Leu Lys Val Leu Ser Thr Thr Thr Met
 1               5                  10                  15 ctg ttg gct tta aca gcc act tct cca gcg ttt tcc tat att act cat     96
Leu Leu Ala Leu Thr Ala Thr Ser Pro Ala Phe Ser Tyr Ile Thr His
             20                  25                  30 gcc gca aat gga ata cat gat gta gaa gat aaa aag aaa gag gat aaa    144
Ala Ala Asn Gly Ile His Asp Val Glu Asp Lys Lys Lys Glu Asp Lys
         35                  40                  45 gaa aaa aaa gag aaa gaa gat aaa gaa aag aaa gag cga gag aaa aaa    192
Glu Lys Lys Glu Lys Glu Asp Lys Glu Lys Lys Glu Arg Glu Lys Lys
     50                  55                  60 gcc aga gaa gaa aga atg aaa gaa att agt aaa gga att gta aca aca    240
Ala Arg Glu Glu Arg Met Lys Glu Ile Ser Lys Gly Ile Val Thr Thr
 65                  70                  75                  80 gag ttt aac agt gaa gaa gaa caa cga tta caa gat acc caa gcc cta    288
Glu Phe Asn Ser Glu Glu Glu Gln Arg Leu Gln Asp Thr Gln Ala Leu
                 85                  90                  95 tta aaa aaa ctt tcg cct gaa gta ttg gaa atg tat gaa aag gtg gga    336
Leu Lys Lys Leu Ser Pro Glu Val Leu Glu Met Tyr Glu Lys Val Gly
            100                 105                 110 gga aaa att cat ctg aca gat aaa agt att gca gaa aat cct act gtc    384
Gly Lys Ile His Leu Thr Asp Lys Ser Ile Ala Glu Asn Pro Thr Val
        115                 120                 125 cgg gat atc agt gaa aaa gaa aag cag ata aaa gat agc gaa gga aat    432
Arg Asp Ile Ser Glu Lys Glu Lys Gln Ile Lys Asp Ser Glu Gly Asn
    130                 135                 140 gaa gtt tcc tta gat tct cat ttt gta ttt tca ata ggt ggt aaa aac    480
```

```
Glu Val Ser Leu Asp Ser His Phe Val Phe Ser Ile Gly Gly Lys Asn
145                 150                 155                 160 cca gct ctg att atc cat aca gaa gag tat tcg gaa agc cac agc aaa      528
Pro Ala Leu Ile Ile His Thr Glu Glu Tyr Ser Glu Ser His Ser Lys
                165                 170                 175 agc aaa gag gta tat tat gag gta gga aaa gca atc gct cgt gac acg      576
Ser Lys Glu Val Tyr Tyr Glu Val Gly Lys Ala Ile Ala Arg Asp Thr
        180                 185                 190 tta gat gaa agt act ttt gca aat gaa gcg ttt tta gat gcg cta cat      624
Leu Asp Glu Ser Thr Phe Ala Asn Glu Ala Phe Leu Asp Ala Leu His
                195                 200                 205 caa gca aaa gca gac gaa gat gca agc gcc tta ctt ctt tca cat cta      672
Gln Ala Lys Ala Asp Glu Asp Ala Ser Ala Leu Leu Leu Ser His Leu
    210                 215                 220 cct cct cat gaa ggt gag tat gat gcc gca tat gtg aaa gaa cac atc      720
Pro Pro His Glu Gly Glu Tyr Asp Ala Ala Tyr Val Lys Glu His Ile
225                 230                 235                 240 aat gag ttt cga gag gtg ttt gca cag gcc ttt gcg tat tat tat gaa      768
Asn Glu Phe Arg Glu Val Phe Ala Gln Ala Phe Ala Tyr Tyr Tyr Glu
                245                 250                 255 cct agt tat aaa cct gtg tta aaa gct tat tca ccg gaa atg ttt agg      816
Pro Ser Tyr Lys Pro Val Leu Lys Ala Tyr Ser Pro Glu Met Phe Arg
        260                 265                 270 tac atg gat gac atg agc aaa aaa gga ttt gag gaa ata aat aag agt      864
Tyr Met Asp Asp Met Ser Lys Lys Gly Phe Glu Glu Ile Asn Lys Ser
                275                 280                 285 tca aat gaa aca caa aaa aca gaa cga aaa gat ttc aaa gaa gat gta      912
Ser Asn Glu Thr Gln Lys Thr Glu Arg Lys Asp Phe Lys Glu Asp Val
    290                 295                 300 aca gca gct gac aag tgg tat agg gaa atg ttt aag caa tat agt caa      960
Thr Ala Ala Asp Lys Trp Tyr Arg Glu Met Phe Lys Gln Tyr Ser Gln
305                 310                 315                 320 aag ctc aaa cct gaa caa aag tca gcc atc caa tta tat acc acg caa     1008
Lys Leu Lys Pro Glu Gln Lys Ser Ala Ile Gln Leu Tyr Thr Thr Gln
                325                 330                 335 aat tat aaa acg atc aat aaa gga tta cga gag gac aat ttg cct gta     1056
Asn Tyr Lys Thr Ile Asn Lys Gly Leu Arg Glu Asp Asn Leu Pro Val
        340                 345                 350 gac aag ata aaa gaa gtg cga gac atg tcg aag gct tta gcc aag tcc     1104
Asp Lys Ile Lys Glu Val Arg Asp Met Ser Lys Ala Leu Ala Lys Ser
                355                 360                 365 cct att tca gaa gca gga gtt gtg tat aga aaa gtt ggg aaa gat gcg     1152
Pro Ile Ser Glu Ala Gly Val Val Tyr Arg Lys Val Gly Lys Asp Ala
    370                 375                 380 cta ggt att gac atc acg act aac ttt aaa aat caa aat gtt gta acg     1200
Leu Gly Ile Asp Ile Thr Thr Asn Phe Lys Asn Gln Asn Val Val Thr
385                 390                 395                 400 aaa ttg aaa aat gac tta gaa ggt tca atc aga gaa gag aaa gct ttt     1248
Lys Leu Lys Asn Asp Leu Glu Gly Ser Ile Arg Glu Glu Lys Ala Phe
                405                 410                 415 ctt agt acc tca gta gcg aac cac ttt agt gaa tcc ttc gat gca aaa     1296
Leu Ser Thr Ser Val Ala Asn His Phe Ser Glu Ser Phe Asp Ala Lys
        420                 425                 430 aca gtt cta ttt aaa ata aat atc cca gaa gga aca cat gct gct tat     1344
Thr Val Leu Phe Lys Ile Asn Ile Pro Glu Gly Thr His Ala Ala Tyr
                435                 440                 445 att ttt gga gac ctt gct acc tac caa gga gaa tcc gaa cta atc ata     1392
Ile Phe Gly Asp Leu Ala Thr Tyr Gln Gly Glu Ser Glu Leu Ile Ile
    450                 455                 460
```

```
gat aaa ggc tct tct tac agg att gat aaa att aat acg tat gaa tac    1440
Asp Lys Gly Ser Ser Tyr Arg Ile Asp Lys Ile Asn Thr Tyr Glu Tyr
465             470                 475                 480 acg aaa aaa tct gga gtt aaa caa aca aat tta cta gta gaa gca aca    1488
Thr Lys Lys Ser Gly Val Lys Gln Thr Asn Leu Leu Val Glu Ala Thr
                485                 490                 495 tta ctt cca agt gat ctt gca gac aat atc aat acg gca gca aaa gag    1536
Leu Leu Pro Ser Asp Leu Ala Asp Asn Ile Asn Thr Ala Ala Lys Glu
        500                 505                 510 ctg gaa aag cat gga ttg aag gat cag caa gat aat ata ttg gaa aaa    1584
Leu Glu Lys His Gly Leu Lys Asp Gln Gln Asp Asn Ile Leu Glu Lys
    515                 520                 525 ttt att gat tta gat gag tct tta tct gat cta gac cga cta tta aaa    1632
Phe Ile Asp Leu Asp Glu Ser Leu Ser Asp Leu Asp Arg Leu Leu Lys
530             535                 540 aaa tcg aat gaa atg aat gaa gaa caa acg cta gaa tat ttt aaa gca    1680
Lys Ser Asn Glu Met Asn Glu Glu Gln Thr Leu Glu Tyr Phe Lys Ala
545             550                 555                 560 att gtt gat aat gtc agt cat gta aat gaa cat gat gct act att cta    1728
Ile Val Asp Asn Val Ser His Val Asn Glu His Asp Ala Thr Ile Leu
                565                 570                 575 aac aca tta tta acg aat agc aaa gaa aat aca gaa ttt act act tgg    1776
Asn Thr Leu Leu Thr Asn Ser Lys Glu Asn Thr Glu Phe Thr Thr Trp
        580                 585                 590 tta gaa gat gta aaa aca atg tac ggg cat att gaa acg ata caa aaa    1824
Leu Glu Asp Val Lys Thr Met Tyr Gly His Ile Glu Thr Ile Gln Lys
    595                 600                 605 tta agc gac aat gaa ata att gat tac cta aca aca tta aaa ggt aaa    1872
Leu Ser Asp Asn Glu Ile Ile Asp Tyr Leu Thr Thr Leu Lys Gly Lys
610             615                 620 tta gac tct gat aac agc taa                                        1893
Leu Asp Ser Asp Asn Ser
625             630

<210> SEQ ID NO 10
<211> LENGTH: 630
<212> TYPE: PRT
<213> ORGANISM: Brevibacillus

<400> SEQUENCE: 10

Met Leu His Arg Asn Lys Met Leu Lys Val Leu Ser Thr Thr Thr Met
1               5                   10                  15

Leu Leu Ala Leu Thr Ala Thr Ser Pro Ala Phe Ser Tyr Ile Thr His
                20                  25                  30

Ala Ala Asn Gly Ile His Asp Val Glu Asp Lys Lys Lys Glu Asp Lys
            35                  40                  45

Glu Lys Lys Glu Lys Glu Asp Lys Glu Lys Lys Glu Arg Glu Lys Lys
        50                  55                  60

Ala Arg Glu Glu Arg Met Lys Glu Ile Ser Lys Gly Ile Val Thr Thr
65                  70                  75                  80

Glu Phe Asn Ser Glu Glu Gln Arg Leu Gln Asp Thr Gln Ala Leu
                85                  90                  95

Leu Lys Lys Leu Ser Pro Glu Val Leu Glu Met Tyr Glu Lys Val Gly
            100                 105                 110

Gly Lys Ile His Leu Thr Asp Lys Ser Ile Ala Glu Asn Pro Thr Val
        115                 120                 125

Arg Asp Ile Ser Glu Lys Glu Lys Gln Ile Lys Asp Ser Glu Gly Asn
    130                 135                 140
```

```
Glu Val Ser Leu Asp Ser His Phe Val Phe Ser Ile Gly Gly Lys Asn
145                 150                 155                 160

Pro Ala Leu Ile Ile His Thr Glu Glu Tyr Ser Glu Ser His Ser Lys
                165                 170                 175

Ser Lys Glu Val Tyr Tyr Glu Val Gly Lys Ala Ile Ala Arg Asp Thr
                180                 185                 190

Leu Asp Glu Ser Thr Phe Ala Asn Glu Ala Phe Leu Asp Ala Leu His
        195                 200                 205

Gln Ala Lys Ala Asp Glu Asp Ala Ser Ala Leu Leu Leu Ser His Leu
210                 215                 220

Pro Pro His Glu Gly Glu Tyr Asp Ala Ala Tyr Val Lys Glu His Ile
225                 230                 235                 240

Asn Glu Phe Arg Glu Val Phe Ala Gln Ala Phe Ala Tyr Tyr Tyr Glu
                245                 250                 255

Pro Ser Tyr Lys Pro Val Leu Lys Ala Tyr Ser Pro Glu Met Phe Arg
                260                 265                 270

Tyr Met Asp Asp Met Ser Lys Lys Gly Phe Glu Glu Ile Asn Lys Ser
        275                 280                 285

Ser Asn Glu Thr Gln Lys Thr Glu Arg Lys Asp Phe Lys Glu Asp Val
290                 295                 300

Thr Ala Ala Asp Lys Trp Tyr Arg Glu Met Phe Lys Gln Tyr Ser Gln
305                 310                 315                 320

Lys Leu Lys Pro Glu Gln Lys Ser Ala Ile Gln Leu Tyr Thr Thr Gln
                325                 330                 335

Asn Tyr Lys Thr Ile Asn Lys Gly Leu Arg Glu Asp Asn Leu Pro Val
        340                 345                 350

Asp Lys Ile Lys Glu Val Arg Asp Met Ser Lys Ala Leu Ala Lys Ser
                355                 360                 365

Pro Ile Ser Glu Ala Gly Val Val Tyr Arg Lys Val Gly Lys Asp Ala
370                 375                 380

Leu Gly Ile Asp Ile Thr Thr Asn Phe Lys Asn Gln Asn Val Val Thr
385                 390                 395                 400

Lys Leu Lys Asn Asp Leu Glu Gly Ser Ile Arg Glu Glu Lys Ala Phe
                405                 410                 415

Leu Ser Thr Ser Val Ala Asn His Phe Ser Glu Ser Phe Asp Ala Lys
        420                 425                 430

Thr Val Leu Phe Lys Ile Asn Ile Pro Glu Gly Thr His Ala Ala Tyr
                435                 440                 445

Ile Phe Gly Asp Leu Ala Thr Tyr Gln Gly Glu Ser Glu Leu Ile Ile
450                 455                 460

Asp Lys Gly Ser Ser Tyr Arg Ile Asp Lys Ile Asn Thr Tyr Glu Tyr
465                 470                 475                 480

Thr Lys Lys Ser Gly Val Lys Gln Thr Asn Leu Leu Val Glu Ala Thr
                485                 490                 495

Leu Leu Pro Ser Asp Leu Ala Asp Asn Ile Asn Thr Ala Ala Lys Glu
        500                 505                 510

Leu Glu Lys His Gly Leu Lys Asp Gln Gln Asp Asn Ile Leu Glu Lys
                515                 520                 525

Phe Ile Asp Leu Asp Glu Ser Leu Ser Asp Leu Asp Arg Leu Leu Lys
        530                 535                 540

Lys Ser Asn Glu Met Asn Glu Glu Gln Thr Leu Glu Tyr Phe Lys Ala
545                 550                 555                 560

Ile Val Asp Asn Val Ser His Val Asn Glu His Asp Ala Thr Ile Leu
```

```
                565                 570                 575
Asn Thr Leu Leu Thr Asn Ser Lys Glu Asn Thr Glu Phe Thr Thr Trp
            580                 585                 590

Leu Glu Asp Val Lys Thr Met Tyr Gly His Ile Glu Thr Ile Gln Lys
            595                 600                 605

Leu Ser Asp Asn Glu Ile Ile Asp Tyr Leu Thr Thr Leu Lys Gly Lys
            610                 615                 620

Leu Asp Ser Asp Asn Ser
625                 630

<210> SEQ ID NO 11
<211> LENGTH: 2287
<212> TYPE: DNA
<213> ORGANISM: Brevibacillus

<400> SEQUENCE: 11
taaacatgaa ggtaatgact gaacctcccg ctatcccaat agatgtcaaa aacagccctc      60
ttttccatag taatcacata atagatgtac taaaaaagag ggctgttttc ttcatttgtc     120
gaggacactg ataaacgagt gattttatct tcgatggata tacaaaagac tctactacct     180 tcggggttc cactacatgt aaggaggaat ttagatgcta cacagaaata aaatgctgaa     240
agtcctgagt acaactacga tgctgttggc tttaacagcc acttctccag cgttttccta     300
tattactcat gccgcaaatg aatacatga tgtagaagat aaaaagaaag aggataaaga     360 aaaaaagag aagaagata agaaaagaa agagcgagag aaaaaagcca gagaagaaag     420
aatgaaagaa attagtaaag gaattgtaac aacagagttt aacagtgaag aagaacaacg     480
attacaagat acccaagccc tattaaaaaa actttcgcct gaagtattgg aaatgtatga     540
aaaggtggga ggaaaaattc atctgacaga taaaagtatt gcagaaaatc ctactgtccg     600
ggatatcagt gaaaagaaa agcagataaa agatagcgaa ggaaatgaag tttccttaga     660
ttctcatttt gtattttcaa taggtggtaa aaacccagct ctgattatcc atacagaaga     720
gtattcggaa agccacagca aaagcaaaga ggtatattat gaggtaggaa aagcaatcgc     780
tcgtgacacg ttagatgaaa gtacttttgc aaatgaagcg tttttagatg cgctacatca     840
agcaaaagca gacgaagatg caagcgcctt acttcttttca catctacctc ctcatgaagg     900
tgagtatgat gccgcatatg tgaaagaaca catcaatgag tttcgagagg tgtttgcaca     960
ggcctttgcg tattattatg aacctagtta taaacctgtg ttaaaagctt attcaccgga    1020
aatgtttagg tacatggatg acatgagcaa aaaaggattt gaggaaataa ataagagttc    1080
aaatgaaaca caaaaaacag aacgaaaaga tttcaaagaa gatgtaacag cagctgacaa    1140
gtggtatagg gaaatgttta agcaaatatag tcaaaagctc aaacctgaac aaaagtcagc    1200
catccaatta tataccacgc aaaattataa aacgatcaat aaaggattac gagaggacaa    1260
tttgcctgta gacaagataa aagaagtgcg agacatgtcg aaggctttag ccaagtcccc    1320
tatttcagaa gcaggagttg tgtatagaaa agttgggaaa gatgcgctag gtattgacat    1380
cacgactaac tttaaaaatc aaaatgttgt aacgaaattg aaaaatgact tagaaggttc    1440
aatcagagaa gagaaagctt ttcttagtac ctcagtagcg aaccactta gtgaatcctt    1500 cgatgcaaaa acagttctat ttaaaataaa tatcccagaa ggaacacatg ctgcttatat    1560
ttttggagac cttgctacct accaaggaga atccgaacta atcatagata aaggctcttc    1620
ttacaggatt gataaaatta atacgtatga atacacgaaa aaatctggag ttaaacaaac    1680
aaatttacta gtagaagcaa cattacttcc aagtgatctt gcagacaata tcaatacggc    1740
```

```
agcaaaagag ctggaaaagc atggattgaa ggatcagcaa gataatatat tggaaaaatt    1800
tattgattta gatgagtctt tatctgatct agaccgacta ttaaaaaaat cgaatgaaat    1860
gaatgaagaa caaacgctag aatattttaa agcaattgtt gataatgtca gtcatgtaaa    1920
tgaacatgat gctactattc taaacacatt attaacgaat agcaaagaaa atacagaatt    1980
tactacttgg ttagaagatg taaaaacaat gtacgggcat attgaaacga tacaaaaatt    2040
aagcgacaat gaaataattg attacctaac aacattaaaa ggtaaattag actctgataa    2100
cagctaaaag aatctaagat gcttttccat actctaagtc attagcgagt atcctcccac    2160
atccagatcg ctgtaaaaat gcaccCctaa cgttcatcgg taaactcaaa aggttttttcc    2220 aatgcctact gaagggtgt attttattta aaagtccaaa ggaatgttgt tatgctgctc    2280
tttcgcg                                                              2287

<210> SEQ ID NO 12
<211> LENGTH: 2031
<212> TYPE: DNA
<213> ORGANISM: Artificial Sequence
<220> FEATURE:
<223> OTHER INFORMATION: synthetic nucleotide sequence
<221> NAME/KEY: CDS
<222> LOCATION: (1)...(2031)

<400> SEQUENCE: 12 atg aac cag aac cag aac cag aac cag aac cag aac aag aat gag ctc      48
Met Asn Gln Asn Gln Asn Gln Asn Gln Asn Gln Asn Lys Asn Glu Leu
1               5                   10                  15 cag atc atc gag cca agc tcc gac agc ttc ctc tac agc cac aac aac      96
Gln Ile Ile Glu Pro Ser Ser Asp Ser Phe Leu Tyr Ser His Asn Asn
            20                  25                  30 tac ccc tac agc acc gac ccc aac acc gtg ctg cat gga agg aac tac     144
Tyr Pro Tyr Ser Thr Asp Pro Asn Thr Val Leu His Gly Arg Asn Tyr
        35                  40                  45 aag gag tgg ctg aac atg tgc acc ggc act gat gat tca aga gga cca     192
Lys Glu Trp Leu Asn Met Cys Thr Gly Thr Asp Asp Ser Arg Gly Pro
    50                  55                  60 gaa gct gct tca aca gca aga agc gcc atc tcc gtc gcc atc acc atc     240
Glu Ala Ala Ser Thr Ala Arg Ser Ala Ile Ser Val Ala Ile Thr Ile
65                  70                  75                  80 tcc acc acc atc ctc ggc ctc ctc ggc gtg cca ttt gca agc cag atc     288
Ser Thr Thr Ile Leu Gly Leu Leu Gly Val Pro Phe Ala Ser Gln Ile
                85                  90                  95 ggc gcc ttc tac aac ttc gtg ctc aac acc gtc tgg cct caa ggc aac     336
Gly Ala Phe Tyr Asn Phe Val Leu Asn Thr Val Trp Pro Gln Gly Asn
            100                 105                 110 aac caa tgg gag gag ttc atg agg cat gtg gag aac ctc atc aat gaa     384
Asn Gln Trp Glu Glu Phe Met Arg His Val Glu Asn Leu Ile Asn Glu
        115                 120                 125 agg atc gcc gac tat gca aga tca aag gcg ctg gcg gag ctc acc ggc     432
Arg Ile Ala Asp Tyr Ala Arg Ser Lys Ala Leu Ala Glu Leu Thr Gly
    130                 135                 140 ctc ggc aac aac ctc aac ctc tac aga gaa gca ttt gaa gat tgg aga     480
Leu Gly Asn Asn Leu Asn Leu Tyr Arg Glu Ala Phe Glu Asp Trp Arg
145                 150                 155                 160 aga aat cca aca agc caa gaa gcc aag aca agg gtg atc gac cgc ttc     528
Arg Asn Pro Thr Ser Gln Glu Ala Lys Thr Arg Val Ile Asp Arg Phe
                165                 170                 175 aga atc ttg gat ggc ctc ttc gag gcc tac atg cca tca ttt gct gtt     576
Arg Ile Leu Asp Gly Leu Phe Glu Ala Tyr Met Pro Ser Phe Ala Val
```

-continued

```
            180                 185                 190
caa gga ttt gag gtg cag ctg ctc acc gtc tac gcc tcc gcc gcc aac        624
Gln Gly Phe Glu Val Gln Leu Leu Thr Val Tyr Ala Ser Ala Ala Asn
        195                 200                 205 atc cac ctc ttc ctg ctg aga gat tca agc atc tat ggg ctg gac tgg        672
Ile His Leu Phe Leu Leu Arg Asp Ser Ser Ile Tyr Gly Leu Asp Trp
    210                 215                 220 ggc ctc agc caa aca aat gtc aat gag aac tac aac agg cag atc cgc        720
Gly Leu Ser Gln Thr Asn Val Asn Glu Asn Tyr Asn Arg Gln Ile Arg
225                 230                 235                 240 cac acc gcc acc tac gcc aac cac tgc acc acc tgg tac caa act ggg        768
His Thr Ala Thr Tyr Ala Asn His Cys Thr Thr Trp Tyr Gln Thr Gly
                245                 250                 255 ctg caa agg ctg caa gga aca aat gca aca agc tgg ggc gcc tac aac        816
Leu Gln Arg Leu Gln Gly Thr Asn Ala Thr Ser Trp Gly Ala Tyr Asn
            260                 265                 270 agg ttc aga agg gag atg aca ttg acg gtg ctg gac atc tca agc ctc        864
Arg Phe Arg Arg Glu Met Thr Leu Thr Val Leu Asp Ile Ser Ser Leu
        275                 280                 285 ttc agc aac tat gac tac aga agc tac cca aca gaa gtt cga gga gag        912
Phe Ser Asn Tyr Asp Tyr Arg Ser Tyr Pro Thr Glu Val Arg Gly Glu
    290                 295                 300 ctg aca agg gag atc tac aca gat cct gtt gga ttt gga tgg cag aac        960
Leu Thr Arg Glu Ile Tyr Thr Asp Pro Val Gly Phe Gly Trp Gln Asn
305                 310                 315                 320 aat gct cct tcc ttc gcc gag att gag aac ctc gcc atc agg gcg cca       1008
Asn Ala Pro Ser Phe Ala Glu Ile Glu Asn Leu Ala Ile Arg Ala Pro
                325                 330                 335 agg acg gtg aca tgg ctc aac tca aca aga atc cac acc ggc acc ttg       1056
Arg Thr Val Thr Trp Leu Asn Ser Thr Arg Ile His Thr Gly Thr Leu
            340                 345                 350 caa gga tgg agc ggc agc aac aga tat tgg gcg gcg cac atg caa aac       1104
Gln Gly Trp Ser Gly Ser Asn Arg Tyr Trp Ala Ala His Met Gln Asn
        355                 360                 365 ttc tca gaa acc aac agc ggc aac ata aga ttt gat ggg ccg ctc tat       1152
Phe Ser Glu Thr Asn Ser Gly Asn Ile Arg Phe Asp Gly Pro Leu Tyr
    370                 375                 380 gga agc acc gtc ggc acc atc atc agg acg gac aac tac gag atg ggc       1200
Gly Ser Thr Val Gly Thr Ile Ile Arg Thr Asp Asn Tyr Glu Met Gly
385                 390                 395                 400 aac agg gac atc tac acc atc acc tcc gag gcc gtc ggc gcg ctg tgg       1248
Asn Arg Asp Ile Tyr Thr Ile Thr Ser Glu Ala Val Gly Ala Leu Trp
                405                 410                 415 cct cat ggc cag acg gtg cta gga gtt gct tca gca agg ttc acc ctc       1296
Pro His Gly Gln Thr Val Leu Gly Val Ala Ser Ala Arg Phe Thr Leu
            420                 425                 430 cgc cac ctc agc aac aac ttc acc caa gtg ctg gtg tat gag aac ccc       1344
Arg His Leu Ser Asn Asn Phe Thr Gln Val Leu Val Tyr Glu Asn Pro
        435                 440                 445 atc agc aac agc ttc aac aga agc acc gtc acc tcc gag ctg cca gga       1392
Ile Ser Asn Ser Phe Asn Arg Ser Thr Val Thr Ser Glu Leu Pro Gly
    450                 455                 460 gaa aat tca gat cgg cca aca gat tct gac tac agc cac cgg ctg acc       1440
Glu Asn Ser Asp Arg Pro Thr Asp Ser Asp Tyr Ser His Arg Leu Thr
465                 470                 475                 480 tgc atc acc gcc ttc cgc gcc ggc aac aat ggc acc gtg ccg gtg ttt       1488
Cys Ile Thr Ala Phe Arg Ala Gly Asn Asn Gly Thr Val Pro Val Phe
                485                 490                 495 gga tgg aca tca agg acg gtg aac agg gac aac atc atc gag cag aac       1536
```

```
Gly Trp Thr Ser Arg Thr Val Asn Arg Asp Asn Ile Ile Glu Gln Asn
                    500                 505                 510 aag atc act caa ttt cct gga gtg aag agc cac acc ctc aac aac tgc      1584
Lys Ile Thr Gln Phe Pro Gly Val Lys Ser His Thr Leu Asn Asn Cys
        515                 520                 525 caa gtg gtg cgc ggc acc ggc ttc acc ggc ggt gat tgg ctg cgg ccc      1632
Gln Val Val Arg Gly Thr Gly Phe Thr Gly Gly Asp Trp Leu Arg Pro
530                 535                 540 aac aac aat ggc acc ttc cgc ctc acc atc acc agc ttc tca agc caa      1680
Asn Asn Asn Gly Thr Phe Arg Leu Thr Ile Thr Ser Phe Ser Ser Gln
545                 550                 555                 560 agc tac agg atc agg ctg cgc tac gcc acc tcc gtc ggc aac acc agc      1728
Ser Tyr Arg Ile Arg Leu Arg Tyr Ala Thr Ser Val Gly Asn Thr Ser
                565                 570                 575 ttg gtg atc tca agc tct gat gct ggc atc agc agc acc acc atc ccg      1776
Leu Val Ile Ser Ser Ser Asp Ala Gly Ile Ser Ser Thr Thr Ile Pro
            580                 585                 590 ctg aca agc acc atc acc tcg ctg ccg cag acg gtg cca tat caa gcc      1824
Leu Thr Ser Thr Ile Thr Ser Leu Pro Gln Thr Val Pro Tyr Gln Ala
        595                 600                 605 ttc cgc gtg gtg gac ctg ccc atc acc ttc acc acg ccg acg acg cag      1872
Phe Arg Val Val Asp Leu Pro Ile Thr Phe Thr Thr Pro Thr Thr Gln
610                 615                 620 agg aac tac acc ttc gac ttc cgc ctc caa aat cca tca aat gca aat      1920
Arg Asn Tyr Thr Phe Asp Phe Arg Leu Gln Asn Pro Ser Asn Ala Asn
625                 630                 635                 640 gtg ttc atc gac aga ttt gaa ttt gtt cca ata gga gga agc ctc tca      1968
Val Phe Ile Asp Arg Phe Glu Phe Val Pro Ile Gly Gly Ser Leu Ser
                645                 650                 655 gaa tat gaa aca aag cac cag ctg gag aag gca agg aag gcc gtc aac      2016
Glu Tyr Glu Thr Lys His Gln Leu Glu Lys Ala Arg Lys Ala Val Asn
            660                 665                 670 gac ctc ttc acc aac                                                  2031
Asp Leu Phe Thr Asn
        675

<210> SEQ ID NO 13
<211> LENGTH: 1929
<212> TYPE: DNA
<213> ORGANISM: Artificial Sequence
<220> FEATURE:
<223> OTHER INFORMATION: synthetic nucleotide sequence
<221> NAME/KEY: CDS
<222> LOCATION: (1)...(1929)

<400> SEQUENCE: 13 atg cca agc agc gac agc ttc ctc tac agc cac aac aac tac ccc tac       48
Met Pro Ser Ser Asp Ser Phe Leu Tyr Ser His Asn Asn Tyr Pro Tyr
1               5                   10                  15 agc aca gat cca aac acc gtg ctg cat gga agg aac tac aag gaa tgg       96
Ser Thr Asp Pro Asn Thr Val Leu His Gly Arg Asn Tyr Lys Glu Trp
            20                  25                  30 ctc aac atg tgc act gga aca gat gat tca aga gga cca gaa gct gct      144
Leu Asn Met Cys Thr Gly Thr Asp Asp Ser Arg Gly Pro Glu Ala Ala
        35                  40                  45 tca aca gca agg agc gcc atc tcc gtc gcc atc acc ata agc acc acc      192
Ser Thr Ala Arg Ser Ala Ile Ser Val Ala Ile Thr Ile Ser Thr Thr
    50                  55                  60 atc ctc ggc ctg ctg gga gtt ccc ttc gcc agc cag atc ggc gcc ttc      240
Ile Leu Gly Leu Leu Gly Val Pro Phe Ala Ser Gln Ile Gly Ala Phe
65                  70                  75                  80
```

```
tac aac ttc gtc ctc aac acc gtc tgg cct caa gga aac aac caa tgg     288
Tyr Asn Phe Val Leu Asn Thr Val Trp Pro Gln Gly Asn Asn Gln Trp
                85                  90                  95 gag gag ttc atg agg cat gtg gag aac ctc atc aat gaa agg att gct     336
Glu Glu Phe Met Arg His Val Glu Asn Leu Ile Asn Glu Arg Ile Ala
                100                 105                 110 gat tat gca aga tca aag gcg ctg gcg gag ctc acc ggc ctc ggc aac     384
Asp Tyr Ala Arg Ser Lys Ala Leu Ala Glu Leu Thr Gly Leu Gly Asn
                115                 120                 125 aac ctc aac ctc tac aga gaa gca ttt gaa gat tgg aga aga aat cca     432
Asn Leu Asn Leu Tyr Arg Glu Ala Phe Glu Asp Trp Arg Arg Asn Pro
        130                 135                 140 aca tca caa gaa gca aaa aca agg gtg atc gac agg ttc aga atc ttg     480
Thr Ser Gln Glu Ala Lys Thr Arg Val Ile Asp Arg Phe Arg Ile Leu
145                 150                 155                 160 gat ggc ctc ttc gag gcc tac atg ccc tcc ttc gcc gtc caa gga ttt     528
Asp Gly Leu Phe Glu Ala Tyr Met Pro Ser Phe Ala Val Gln Gly Phe
                165                 170                 175 gag gtg cag ctg ctc acc gtc tat gct tct gct gcc aac atc cac ctc     576
Glu Val Gln Leu Leu Thr Val Tyr Ala Ser Ala Ala Asn Ile His Leu
                180                 185                 190 ttc ctg ctg aga gat tca agc atc tat ggc ctg gac tgg ggc ttg agc     624
Phe Leu Leu Arg Asp Ser Ser Ile Tyr Gly Leu Asp Trp Gly Leu Ser
                195                 200                 205 caa aca aat gtc aat gag aac tac aac agg cag atc cgc cac aca gca     672
Gln Thr Asn Val Asn Glu Asn Tyr Asn Arg Gln Ile Arg His Thr Ala
        210                 215                 220 aca tat gcc aac cac tgc acc acc tgg tat caa act ggc ctc cag agg     720
Thr Tyr Ala Asn His Cys Thr Thr Trp Tyr Gln Thr Gly Leu Gln Arg
225                 230                 235                 240 ctg caa gga aca aat gca aca agc tgg ggc gcc tac aac agg ttc aga     768
Leu Gln Gly Thr Asn Ala Thr Ser Trp Gly Ala Tyr Asn Arg Phe Arg
                245                 250                 255 agg gag atg acc ctc acc gtg ctg gac atc agc agc ctc ttc tca aac     816
Arg Glu Met Thr Leu Thr Val Leu Asp Ile Ser Ser Leu Phe Ser Asn
                260                 265                 270 tat gac tac aga agc tac cca aca gaa gtt cga gga gag ctg aca agg     864
Tyr Asp Tyr Arg Ser Tyr Pro Thr Glu Val Arg Gly Glu Leu Thr Arg
                275                 280                 285 gag atc tac aca gat cct gtt gga ttt gga tgg cag aac aat gct cct     912
Glu Ile Tyr Thr Asp Pro Val Gly Phe Gly Trp Gln Asn Asn Ala Pro
        290                 295                 300 tct ttt gct gaa att gag aac ctc gcc atc aga gct cca agg acg gtg     960
Ser Phe Ala Glu Ile Glu Asn Leu Ala Ile Arg Ala Pro Arg Thr Val
305                 310                 315                 320 aca tgg ctg aac tca aca aga atc cac acc ggc acc ctc caa gga tgg    1008
Thr Trp Leu Asn Ser Thr Arg Ile His Thr Gly Thr Leu Gln Gly Trp
                325                 330                 335 agc ggc agc aac aga tat tgg gcg gcg cac atg caa aac ttc tca gaa    1056
Ser Gly Ser Asn Arg Tyr Trp Ala Ala His Met Gln Asn Phe Ser Glu
                340                 345                 350 aca aac agc ggc aac atc aga ttt gat ggg ccg ctc tat gga agc acc    1104
Thr Asn Ser Gly Asn Ile Arg Phe Asp Gly Pro Leu Tyr Gly Ser Thr
        355                 360                 365 gtc ggc acc atc atc agg aca gac aac tat gag atg ggc aac agg gac    1152
Val Gly Thr Ile Ile Arg Thr Asp Asn Tyr Glu Met Gly Asn Arg Asp
370                 375                 380 atc tac acc ata aca tca gaa gct gtt gga gct ctc tgg cct cat ggc    1200
Ile Tyr Thr Ile Thr Ser Glu Ala Val Gly Ala Leu Trp Pro His Gly
385                 390                 395                 400
```

```
caa aca gtg ctg ggc gtc gcc tct gca agg ttc acc ctc cgc cac ctc      1248
Gln Thr Val Leu Gly Val Ala Ser Ala Arg Phe Thr Leu Arg His Leu
            405                 410                 415 tcc aac aac ttc acc cag gtg ctg gtg tat gag aac ccc atc agc aac      1296
Ser Asn Asn Phe Thr Gln Val Leu Val Tyr Glu Asn Pro Ile Ser Asn
        420                 425                 430 agc ttc aac aga agc acc gtg aca tca gag ctg cca gga gaa aac agc      1344
Ser Phe Asn Arg Ser Thr Val Thr Ser Glu Leu Pro Gly Glu Asn Ser
    435                 440                 445 gac cgg cca aca gat tct gac tac agc cac cgc ctc acc tgc atc acc      1392
Asp Arg Pro Thr Asp Ser Asp Tyr Ser His Arg Leu Thr Cys Ile Thr
450                 455                 460 gcc ttc aga gct ggc aac aat gga aca gtt cct gtt ttt gga tgg aca      1440
Ala Phe Arg Ala Gly Asn Asn Gly Thr Val Pro Val Phe Gly Trp Thr
465                 470                 475                 480 tca agg acg gtg aac agg gac aac atc atc gag cag aac aag atc act      1488
Ser Arg Thr Val Asn Arg Asp Asn Ile Ile Glu Gln Asn Lys Ile Thr
            485                 490                 495 cag ttc ccc ggc gtc aag agc cac acc ctc aac aac tgc cag gtg gtt      1536
Gln Phe Pro Gly Val Lys Ser His Thr Leu Asn Asn Cys Gln Val Val
        500                 505                 510 aga gga act ggc ttc act gga gga gat tgg ctg cgg cca aac aac aat      1584
Arg Gly Thr Gly Phe Thr Gly Gly Asp Trp Leu Arg Pro Asn Asn Asn
    515                 520                 525 ggc acc ttc cgc ctc acc atc acc agc ttc tca agc caa agc tac agg      1632
Gly Thr Phe Arg Leu Thr Ile Thr Ser Phe Ser Ser Gln Ser Tyr Arg
530                 535                 540 atc agg ctg aga tat gca act tct gtt ggt aac acc agc ttg gtg atc      1680
Ile Arg Leu Arg Tyr Ala Thr Ser Val Gly Asn Thr Ser Leu Val Ile
545                 550                 555                 560 tcc tcc tca gat gct ggc atc tcc tcc acc atc ccc ctc acc tcc          1728
Ser Ser Ser Asp Ala Gly Ile Ser Ser Thr Ile Pro Leu Thr Ser
            565                 570                 575 acc atc acc agc ctt cct caa aca gtt cca tat caa gcc ttc cgc gtg      1776
Thr Ile Thr Ser Leu Pro Gln Thr Val Pro Tyr Gln Ala Phe Arg Val
        580                 585                 590 gta gat ctt ccc atc acc ttc acc acc ccc acc acc caa agg aac tac      1824
Val Asp Leu Pro Ile Thr Phe Thr Thr Pro Thr Thr Gln Arg Asn Tyr
    595                 600                 605 acc ttt gat ttc cgc ctc caa aat cca agc aat gca aat gtt ttc atc      1872
Thr Phe Asp Phe Arg Leu Gln Asn Pro Ser Asn Ala Asn Val Phe Ile
610                 615                 620 gac aga ttt gaa ttt gtt cca att gga gga agc ctc tca gaa tat gaa      1920
Asp Arg Phe Glu Phe Val Pro Ile Gly Gly Ser Leu Ser Glu Tyr Glu
625                 630                 635                 640 aca aag cac                                                          1929
Thr Lys His <210> SEQ ID NO 14
<211> LENGTH: 1056
<212> TYPE: DNA
<213> ORGANISM: Artificial Sequence
<220> FEATURE:
<223> OTHER INFORMATION: synthetic nucleotide sequence
<221> NAME/KEY: CDS
<222> LOCATION: (1)...(1056)

<400> SEQUENCE: 14 atg atg gag cca atg aag ttc aga aaa aat ggc ctc tac aac atc gtc       48
Met Met Glu Pro Met Lys Phe Arg Lys Asn Gly Leu Tyr Asn Ile Val
1               5                   10                  15
```

| | | |
|---|---|---|
| aat gtc aac agc ggc aac ctc gcc gtg gtg aag gat gct tca aag gag<br>Asn Val Asn Ser Gly Asn Leu Ala Val Val Lys Asp Ala Ser Lys Glu<br>20 25 30 | 96 | |
| aac tat gct ccc atc atc cag ttc gac aag aga gga aca gac aat gag<br>Asn Tyr Ala Pro Ile Ile Gln Phe Asp Lys Arg Gly Thr Asp Asn Glu<br>35 40 45 | 144 | |
| aag ttt gtt ttc ttc ccg ctg gac agc aag ggc aag agc caa aca tat<br>Lys Phe Val Phe Phe Pro Leu Asp Ser Lys Gly Lys Ser Gln Thr Tyr<br>50 55 60 | 192 | |
| gcc att gct gcc tac cac agc ggc aag atc atc tgc gtg aag gat gct<br>Ala Ile Ala Ala Tyr His Ser Gly Lys Ile Ile Cys Val Lys Asp Ala<br>65 70 75 80 | 240 | |
| tca aca gag aac tat gct ccc atc atc cag ttc aac tgg aac aac acc<br>Ser Thr Glu Asn Tyr Ala Pro Ile Ile Gln Phe Asn Trp Asn Asn Thr<br>85 90 95 | 288 | |
| acc aat gag caa tgg aac atc atc cct gac aac agc tgg ggc tac aac<br>Thr Asn Glu Gln Trp Asn Ile Ile Pro Asp Asn Ser Trp Gly Tyr Asn<br>100 105 110 | 336 | |
| atc gtc aac cag aac agc ggc aac ctc gcc gtg gtg aag gat gca agc<br>Ile Val Asn Gln Asn Ser Gly Asn Leu Ala Val Val Lys Asp Ala Ser<br>115 120 125 | 384 | |
| aag gag aac tat gct ccc atc atc cag ttc gac aag aga gga aca atg<br>Lys Glu Asn Tyr Ala Pro Ile Ile Gln Phe Asp Lys Arg Gly Thr Met<br>130 135 140 | 432 | |
| aat gaa gat tgg aag ttc caa gaa gtt tca tgg ttc cct gtt cca gaa<br>Asn Glu Asp Trp Lys Phe Gln Glu Val Ser Trp Phe Pro Val Pro Glu<br>145 150 155 160 | 480 | |
| acg ccg acg gtg gaa acc ctc ccc aag gcg ccg cag ttc aat gat gtt<br>Thr Pro Thr Val Glu Thr Leu Pro Lys Ala Pro Gln Phe Asn Asp Val<br>165 170 175 | 528 | |
| cat caa aat ctt cct cag gtg aca gat gag atc ctc act gga tat gcc<br>His Gln Asn Leu Pro Gln Val Thr Asp Glu Ile Leu Thr Gly Tyr Ala<br>180 185 190 | 576 | |
| atg atc ccc tgc atc atg gtg aga gat cac aac tgg agt gat gaa agc<br>Met Ile Pro Cys Ile Met Val Arg Asp His Asn Trp Ser Asp Glu Ser<br>195 200 205 | 624 | |
| aag atg aaa act tct cca tac tac atc ctc aag aag tac cag ttc tgg<br>Lys Met Lys Thr Ser Pro Tyr Tyr Ile Leu Lys Lys Tyr Gln Phe Trp<br>210 215 220 | 672 | |
| gag ctg ctg gca tca ttc cag ctc ttc aat gga gaa acc cag aag agg<br>Glu Leu Leu Ala Ser Phe Gln Leu Phe Asn Gly Glu Thr Gln Lys Arg<br>225 230 235 240 | 720 | |
| acc tac aag gtg ggg atg aac atg aca gat caa aga agc atg gag aac<br>Thr Tyr Lys Val Gly Met Asn Met Thr Asp Gln Arg Ser Met Glu Asn<br>245 250 255 | 768 | |
| agc atc ggc acc atg att gga gct gat gct ggc ttc cag ttt gat ggc<br>Ser Ile Gly Thr Met Ile Gly Ala Asp Ala Gly Phe Gln Phe Asp Gly<br>260 265 270 | 816 | |
| ctc acc gac gcc atc aag agc gag atc acc acc agc ttg aag gtg gcc<br>Leu Thr Asp Ala Ile Lys Ser Glu Ile Thr Thr Ser Leu Lys Val Ala<br>275 280 285 | 864 | |
| atc tca aga gaa aca aag ctg atg aca gaa gaa act gga gaa gtc atc<br>Ile Ser Arg Glu Thr Lys Leu Met Thr Glu Glu Thr Gly Glu Val Ile<br>290 295 300 | 912 | |
| agg gag aac aag aca ggg aag ctg caa gcc tat gct gaa tat gtc tgc<br>Arg Glu Asn Lys Thr Gly Lys Leu Gln Ala Tyr Ala Glu Tyr Val Cys<br>305 310 315 320 | 960 | |
| gtc agc aag ttc gtg ctg gag agg aca gat gga aca gag gtg gca agc<br>Val Ser Lys Phe Val Leu Glu Arg Thr Asp Gly Thr Glu Val Ala Ser | 1008 | |

```
                   325                 330                 335
tgg acc atg agc aac ccc aac acc atc agc aag acg gtg ttc cct gga    1056
Trp Thr Met Ser Asn Pro Asn Thr Ile Ser Lys Thr Val Phe Pro Gly
            340                 345                 350

<210> SEQ ID NO 15
<211> LENGTH: 1890
<212> TYPE: DNA
<213> ORGANISM: Artificial Sequence
<220> FEATURE:
<223> OTHER INFORMATION: synthetic nucleotide sequence
<221> NAME/KEY: CDS
<222> LOCATION: (1)...(1890)

<400> SEQUENCE: 15 atg ctg cac agg aac aag atg ctg aag gtg ctc tcc acc acc acc atg      48
Met Leu His Arg Asn Lys Met Leu Lys Val Leu Ser Thr Thr Thr Met
 1               5                  10                  15 ctg ctg gcg ctc acc gcc acc tcg ccg gcc ttc tca tac atc acc cat      96
Leu Leu Ala Leu Thr Ala Thr Ser Pro Ala Phe Ser Tyr Ile Thr His
                20                  25                  30 gct gca aat ggc att cat gat gtg gag gac aag aag aag gag gac aag     144
Ala Ala Asn Gly Ile His Asp Val Glu Asp Lys Lys Lys Glu Asp Lys
            35                  40                  45 gag aag aag gag aag gag gac aag gag aag aag gag agg gag aag aag     192
Glu Lys Lys Glu Lys Glu Asp Lys Glu Lys Lys Glu Arg Glu Lys Lys
        50                  55                  60 gca aga gaa gaa agg atg aag gag atc agc aag ggc atc gtc acc acc     240
Ala Arg Glu Glu Arg Met Lys Glu Ile Ser Lys Gly Ile Val Thr Thr
 65                  70                  75                  80 gag ttc aac tca gaa gaa gag cag agg ctg caa gac act caa gct ctg     288
Glu Phe Asn Ser Glu Glu Glu Gln Arg Leu Gln Asp Thr Gln Ala Leu
                85                  90                  95 ctg aag aag ctc tcg ccg gag gtg ctg gag atg tat gag aag gtt gga     336
Leu Lys Lys Leu Ser Pro Glu Val Leu Glu Met Tyr Glu Lys Val Gly
                100                 105                 110 gga aag atc cac ctc acc gac aag agc att gct gag aac ccc acc gtc     384
Gly Lys Ile His Leu Thr Asp Lys Ser Ile Ala Glu Asn Pro Thr Val
            115                 120                 125 agg gac atc tca gag aag gag aag cag atc aag gat tca gaa gga aat     432
Arg Asp Ile Ser Glu Lys Glu Lys Gln Ile Lys Asp Ser Glu Gly Asn
        130                 135                 140 gaa gtt tct ctg gat tct cat ttt gtt ttc tcc atc ggc ggc aag aac     480
Glu Val Ser Leu Asp Ser His Phe Val Phe Ser Ile Gly Gly Lys Asn
145                 150                 155                 160 ccg gcg ctg atc atc cac aca gaa gaa tat tca gaa agc cac agc aag     528
Pro Ala Leu Ile Ile His Thr Glu Glu Tyr Ser Glu Ser His Ser Lys
                165                 170                 175 agc aag gag gtg tac tac gag gtg ggc aag gcc att gca agg gac acc     576
Ser Lys Glu Val Tyr Tyr Glu Val Gly Lys Ala Ile Ala Arg Asp Thr
                180                 185                 190 ttg gat gaa agc acc ttc gcc aat gaa gcc ttc ctg gat gct ctt cat     624
Leu Asp Glu Ser Thr Phe Ala Asn Glu Ala Phe Leu Asp Ala Leu His
            195                 200                 205 caa gca aaa gct gat gaa gat gct tca gct ctg ctg ctg agc cat ctt     672
Gln Ala Lys Ala Asp Glu Asp Ala Ser Ala Leu Leu Leu Ser His Leu
        210                 215                 220 cct cct cat gaa gga gaa tat gat gct gca tat gtc aag gag cac atc     720
Pro Pro His Glu Gly Glu Tyr Asp Ala Ala Tyr Val Lys Glu His Ile
225                 230                 235                 240 aat gag ttc aga gaa gtt ttt gct caa gcc ttc gcc tac tac tac gag     768
Asn Glu Phe Arg Glu Val Phe Ala Gln Ala Phe Ala Tyr Tyr Tyr Glu
```

```
                Asn Glu Phe Arg Glu Val Phe Ala Gln Ala Phe Ala Tyr Tyr Tyr Glu
                                245                 250                 255 cca tca tac aag ccg gtg ctg aag gcc tac tcg ccg gag atg ttc aga        816
Pro Ser Tyr Lys Pro Val Leu Lys Ala Tyr Ser Pro Glu Met Phe Arg
            260                 265                 270 tac atg gat gac atg agc aag aag ggc ttc gag gag atc aac aag agc        864
Tyr Met Asp Asp Met Ser Lys Lys Gly Phe Glu Glu Ile Asn Lys Ser
        275                 280                 285 agc aat gaa aca caa aaa aca gaa agg aag gac ttc aag gaa gat gtc        912
Ser Asn Glu Thr Gln Lys Thr Glu Arg Lys Asp Phe Lys Glu Asp Val
    290                 295                 300 acc gcc gcc gac aaa tgg tac agg gag atg ttc aag cag tac agc cag        960
Thr Ala Ala Asp Lys Trp Tyr Arg Glu Met Phe Lys Gln Tyr Ser Gln
305                 310                 315                 320 aag ctg aag cca gag cag aaa tca gcc atc cag ctc tac acc acc cag       1008
Lys Leu Lys Pro Glu Gln Lys Ser Ala Ile Gln Leu Tyr Thr Thr Gln
                325                 330                 335 aac tac aag acc atc aac aag ggc ctc agg gag gac aac ctt cct gtt       1056
Asn Tyr Lys Thr Ile Asn Lys Gly Leu Arg Glu Asp Asn Leu Pro Val
            340                 345                 350 gac aag atc aag gag gtg agg gac atg agc aag gcg ctg gcc aag agc       1104
Asp Lys Ile Lys Glu Val Arg Asp Met Ser Lys Ala Leu Ala Lys Ser
        355                 360                 365 ccc atc tca gaa gct gga gtg gtg tac agg aag gtg ggc aag gat gct       1152
Pro Ile Ser Glu Ala Gly Val Val Tyr Arg Lys Val Gly Lys Asp Ala
    370                 375                 380 ctt ggc atc gac atc acc acc aac ttc aag aat caa aat gtt gtc acc       1200
Leu Gly Ile Asp Ile Thr Thr Asn Phe Lys Asn Gln Asn Val Val Thr
385                 390                 395                 400 aag ctg aag aat gat ctg gaa gga agc atc agg gag gag aag gcc ttc       1248
Lys Leu Lys Asn Asp Leu Glu Gly Ser Ile Arg Glu Glu Lys Ala Phe
                405                 410                 415 ctc tcc acc tcc gtc gcc aac cac ttc tca gag agc ttt gat gca aaa       1296
Leu Ser Thr Ser Val Ala Asn His Phe Ser Glu Ser Phe Asp Ala Lys
            420                 425                 430 aca gtg ctc ttc aag atc aac atc cca gaa gga aca cat gct gcc tac       1344
Thr Val Leu Phe Lys Ile Asn Ile Pro Glu Gly Thr His Ala Ala Tyr
        435                 440                 445 atc ttt gga gat ctg gcc acc tac caa gga gaa agc gag ctg atc atc       1392
Ile Phe Gly Asp Leu Ala Thr Tyr Gln Gly Glu Ser Glu Leu Ile Ile
    450                 455                 460 gac aaa gga agc agc tac agg atc gac aag atc aac aca tat gag tac       1440
Asp Lys Gly Ser Ser Tyr Arg Ile Asp Lys Ile Asn Thr Tyr Glu Tyr
465                 470                 475                 480 acc aag aag agc ggc gtg aag caa aca aac ctg ctg gtg gag gcc acc       1488
Thr Lys Lys Ser Gly Val Lys Gln Thr Asn Leu Leu Val Glu Ala Thr
                485                 490                 495 ctg ctg cca tca gat ctt gct gac aac atc aac acc gcc gcc aag gag       1536
Leu Leu Pro Ser Asp Leu Ala Asp Asn Ile Asn Thr Ala Ala Lys Glu
            500                 505                 510 ctg gag aag cat ggc ctc aag gat cag cag gac aac atc ctg gag aag       1584
Leu Glu Lys His Gly Leu Lys Asp Gln Gln Asp Asn Ile Leu Glu Lys
        515                 520                 525 ttc atc gac ctg gat gaa agc ctc tca gat ctg gac agg ctg ctg aag       1632
Phe Ile Asp Leu Asp Glu Ser Leu Ser Asp Leu Asp Arg Leu Leu Lys
    530                 535                 540 aag agc aat gag atg aat gag gag cag acg ctg gag tac ttc aag gcc       1680
Lys Ser Asn Glu Met Asn Glu Glu Gln Thr Leu Glu Tyr Phe Lys Ala
545                 550                 555                 560
```

-continued

```
atc gtg gac aat gtt tct cat gtc aat gaa cat gat gcc acc atc ctc    1728
Ile Val Asp Asn Val Ser His Val Asn Glu His Asp Ala Thr Ile Leu
            565             570                 575 aac acc ctc ctc acc aac tca aag gag aac aca gag ttc acc acc tgg    1776
Asn Thr Leu Leu Thr Asn Ser Lys Glu Asn Thr Glu Phe Thr Thr Trp
            580             585                 590 ctg gag gat gtc aag acc atg tat ggc cac att gaa acc atc cag aag    1824
Leu Glu Asp Val Lys Thr Met Tyr Gly His Ile Glu Thr Ile Gln Lys
        595             600                 605 ctc tcc gac aat gag atc atc gac tac ctc acc acc ttg aag ggc aag    1872
Leu Ser Asp Asn Glu Ile Ile Asp Tyr Leu Thr Thr Leu Lys Gly Lys
        610             615             620 ctg gac agc gac aac agc                                             1890
Leu Asp Ser Asp Asn Ser
625             630
```